(12) United States Patent
Kakizawa et al.

(10) Patent No.: US 8,431,161 B2
(45) Date of Patent: Apr. 30, 2013

(54) MICROPARTICLE AND PHARMACEUTICAL COMPOSITION THEREOF

(75) Inventors: Yoshinori Kakizawa, Kanagawa (JP); Reiji Nishio, Kanagawa (JP); Junji Michizoe, Shiga (JP); Masakazu Koiwa, Shiga (JP); Nobuo Ida, Kanagawa (JP); Taisuke Hirano, Kanagawa (JP); Yoichiro Koshi, Kanagawa (JP)

(73) Assignee: Toray Industries, Inc. (JP)

( * ) Notice: Subject to any disclaimer, the term of this patent is extended or adjusted under 35 U.S.C. 154(b) by 41 days.

(21) Appl. No.: 12/867,900

(22) PCT Filed: Feb. 20, 2009

(86) PCT No.: PCT/JP2009/052951
§ 371 (c)(1),
(2), (4) Date: Sep. 15, 2010

(87) PCT Pub. No.: WO2009/104706
PCT Pub. Date: Aug. 27, 2009

(65) Prior Publication Data
US 2011/0003007 A1  Jan. 6, 2011

(30) Foreign Application Priority Data

Feb. 22, 2008 (JP) ................. 2008-041298
Feb. 22, 2008 (JP) ................. 2008-041299
Jun. 26, 2008 (JP) ................. 2008-167026
Jun. 26, 2008 (JP) ................. 2008-167027
Sep. 24, 2008 (JP) ................. 2008-243931
Sep. 24, 2008 (JP) ................. 2008-243932

(51) Int. Cl.
*A61K 9/16* (2006.01)
*A61K 38/27* (2006.01)
*A61K 38/28* (2006.01)
*A61K 38/17* (2006.01)
*A61K 31/721* (2006.01)

(52) U.S. Cl.
USPC ........... 424/499; 424/489; 514/11.4; 514/5.9; 514/7.2; 514/59

(58) Field of Classification Search .................. 424/499, 424/489; 514/5.9, 11.4, 7.2, 777
See application file for complete search history.

(56) References Cited

U.S. PATENT DOCUMENTS

2008/0145432 A1* 6/2008 Kakizawa et al. ............ 424/489

FOREIGN PATENT DOCUMENTS

| EP | 1857489 | * | 11/2007 |
| JP | 60-076531 A | | 5/1985 |
| JP | 10-511957 T | | 11/1998 |
| JP | 2000-501084 T | | 2/2000 |
| JP | 2004-513154 T | | 4/2004 |
| JP | 2004-514734 T | | 5/2004 |
| JP | 2004-521152 T | | 7/2004 |
| WO | WO 96/20698 | * | 7/1996 |
| WO | 2006/095668 A1 | | 9/2006 |
| WO | WO 2006/095668 | * | 9/2006 |

OTHER PUBLICATIONS

Ya-Ping Li et al., "PEGylated PLGA nanoparticles as protein carriers: synthesis, preparation and biodistribution in rats," Journal of Controlled Release, vol. 71, No. 2, 2001, pp. 203-211.

Tatsuro Ouchi et al., "Modification of polylactide upon physical properties by solution-cast blends from polylactide and polylactide-grafted dextran," Polymer, vol. 44, No. 14, 2003, pp. 3927-3933.

Tatsuro Ouchi et al., "Encapsulation and/or Release Behavior of Bovine Serum Albumin within and from Polylactide-Grafted Dextran Microspheres," Macromolecular Bioscience, vol. 4, 2004, pp. 458-463.

Anshu Yang et al., "Tumor necrosis factor alpha blocking peptide loaded PEG-PLGA nanoparticles: Preparation and in vitro evaluation," International Journal of Pharmaceutics, vol. 331, 2007, pp. 123-132.

* cited by examiner

*Primary Examiner* — Anoop Singh
*Assistant Examiner* — Anna Falkowitz
(74) *Attorney, Agent, or Firm* — DLA Piper LLP (US)

(57) ABSTRACT

A microparticle includes an agglomerate of a hydrophilic active substance containing particle, which particle includes an amphiphilic polymer composed of a hydrophobic segment of poly(hydroxy acid) and a hydrophilic segment of polysaccharides or polyethylene glycol, and a hydrophilic active substance. It is characterized by an efficient inclusion of the hydrophilic active substance, and a release of the hydrophilic active substance at an appropriate speed in the human body, and is hence very useful as a DDS pharmaceutical preparation.

22 Claims, 11 Drawing Sheets

Right after preparation 13 days later

Right after preparation 21 days later

MICROPARTICLE AND PHARMACEUTICAL COMPOSITION THEREOF

RELATED APPLICATIONS

This is a §371 of International Application No. PCT/JP2009/052951, with an international filing date of Feb. 20, 2009 (WO 2009/104706 A1, published Aug. 27, 2009), which is based on Japanese Patent Application Nos. 2008-041298, filed Feb. 22, 2008, 2008-041299, filed Feb. 22, 2008, 2008-167026, filed Jun. 26, 2008, 2008-167027, filed Jun. 26, 2008, 2008-243931, filed Sep. 24, 2008, and 2008-243932, filed Sep. 24, 2008, the subject matter of which is incorporated by reference.

TECHNICAL FIELD

This disclosure relates to a microparticle comprising an agglomerate of particles containing hydrophilic active substances, and a pharmaceutical composition thereof. Particularly, the disclosure relates to a microparticle and a pharmaceutical composition thereof as so-called drug delivery system. More particularly, for example, the disclosure relates to a microparticle effectively containing a protein, a peptide drugs, a nucleic acid drugs, and the like of hydrophilic property and large molecular weight, and a pharmaceutical composition thereof.

BACKGROUND

Particulate preparations having drugs enclosed in fine particles called nanoparticle, microparticle, nanosphere, microsphere, or microcapsule are developed, and are attempted to be used as sustained-release agents for drugs.

Particulate preparations using polymer compounds as the base include fine particles composed of biodegradable polylactic acid or poly(lactic acid-glycolic acid). In these particulate preparations, it is hard to encapsulate a protein or a peptide drug of hydrophilic property and large molecular weight while maintaining the bioactivity. In addition, when administering in the human body, it is known that the drug is massively released in a short time, and this phenomenon is called an initial burst.

As fine particles composed of a polymer of covalent bonding of saccharide and poly(hydroxy acid), JP 8-19226 discloses a microcapsule for carrying a pharmacologically active substance composed of a reaction product of polyol and polylactic acid. In this technique, polysaccharides are not used, and nothing is mentioned about inclusion of peptide or protein. The microcapsule manufactured by a spray drying method released the encapsulated drug by 62% in 24 hours. This release speed is too fast, and the microcapsule can be hardly applied as a sustained-release agent for a drug.

JP 2004-521152 and Yuichi Ohya et al., "Encapsulation and/or Release Behavior of Bovine Serum Albumin within and from Polylactide-Grafted Dextran Microsphers," Macromolecular Bioscience, 2004, Vol. 4, pp. 458-463 disclose a nanoparticle or a nanoparticle composed of a material having a biodegradable polymer grafted in polysaccharides, but these literatures mention nothing about a microparticle composed of nanoparticles. JP 2004-521152 discloses, for example, a double emulsion method already cited in other literatures, as a manufacturing method of a microparticle for encapsulating a hydrophilic active substance, but there is no specific description, and inclusion of a drug into a particle, or release of a drug from a particle is not realized. Yuichi Ohya et al., "Encapsulation and/or Release Behavior of Bovine Serum Albumin within and from Polylactide-Grafted Dextran Microsphers," Macromolecular Bioscience, 2004, Vol. 4, pp. 458-463 discloses a microparticle encapsulating an albumin manufactured by the double emulsion method, but the encapsulation efficiency to the included amount of the albumin is 53% or less, and the low encapsulation efficiency of the hydrophilic active substance has a problem in the manufacturing cost.

WO 2006/095668 discloses a fine particle containing an amphiphilic polymer composed of polysaccharides and an aliphatic polyester, more specifically a fine particle composed of an inner nucleus of polysaccharides, a hydrophobic outer layer of aliphatic polyester, and a surface modifier bonded to the hydrophobic outer layer. This fine particle does not have an agglomeration structure of fine particles, and specific examples are not shown about particles of particle diameter of micrometer units. The encapsulation efficiency of the hydrophilic substance is 50% or less, and this low encapsulation efficiency is a similar problem as in the case above.

JP 10-511957 discloses a nanoparticle of average particle diameter of less than 300 nm, composed of a naturally derived polymer of dextran, but specific examples are not shown. This is not an agglomeration structure of fine particles, and the average particle diameter is hundreds of nanometers, and the drug is likely to diffuse from the site of administration, and it is not preferred as a sustained-release agent.

As the polymer for forming particles, JP 2004-513154 and JP 2004-514734 disclose and suggest use of an amphiphilic block polymer having a hydrophilic portion such as polyethylene glycol, and a hydrophobic portion such as poly(lactic acid-glycolic acid). Micelle particles using such amphiphilic block polymer are usually hydrophobic in the inside, and hydrophilic in the outer layer, and they are suited to containment of hydrophobic low molecular weight drugs, but not suited to containment of hydrophilic active substances such as protein or peptide.

JP 2000-501084 and Anshu Yang et al., "Tumor necrosis factor alpha blocking peptide loaded PEG-PLGA nanopeptides: Preferparation and in vitro evaluation," International Journal of Pharmaceutics, 2007, Vol. 331, pp. 123-132 disclose attempts to contain a protein in a particle using an amphiphilic block polymer, but the amount of the drug to be contained is small, or the initial burst is large, and so far the manufacturing technology of particles having properties suited as sustained-release injection of a hydrophilic drug is not established yet.

As mentioned above, microparticles using a polymer have been developed. Hence, it could be helpful to provide a microparticle capable of encapsulating a hydrophilic active substance efficiently, and more particularly a microparticle capable of releasing the encapsulated drug at an appropriate speed, without causing significant initial burst.

SUMMARY

We provide:
a microparticle including an agglomerate of hydrophilic active substance containing particles, which particle includes an amphiphilic polymer composed of a hydrophobic segment of poly(hydroxy acid) and a hydrophilic segment of polysaccharides or polyethylene glycol, and a hydrophilic active substance, or more particularly a microparticle comprising agglomerate of hydrophilic active substance containing particles, which particle has a hydrophilic segment of an amphiphilic polymer in the inside and has an outer layer of the hydrophobic segment of the amphiphilic polymer;

a method for manufacturing a microparticle including forming a reversed-phase emulsion by mixing an aqueous solvent containing a hydrophilic active substance and a water-immiscible organic solvent dissolving an amphiphilic polymer, obtaining a solid content containing a hydrophilic active substance by removing the solvent from the reversed-phase emulsion, and introducing the solid content or a dispersion liquid containing the solid content into a liquid phase containing a surface modifier; and a pharmaceutical preparation including the microparticles.

The microparticle is capable of encapsulating a hydrophilic active substance efficiently, and releasing the hydrophilic active substance at an appropriate speed in the human body, and is hence usable as a novel DDS preparation.

DETAILED DESCRIPTION

Figure 1:
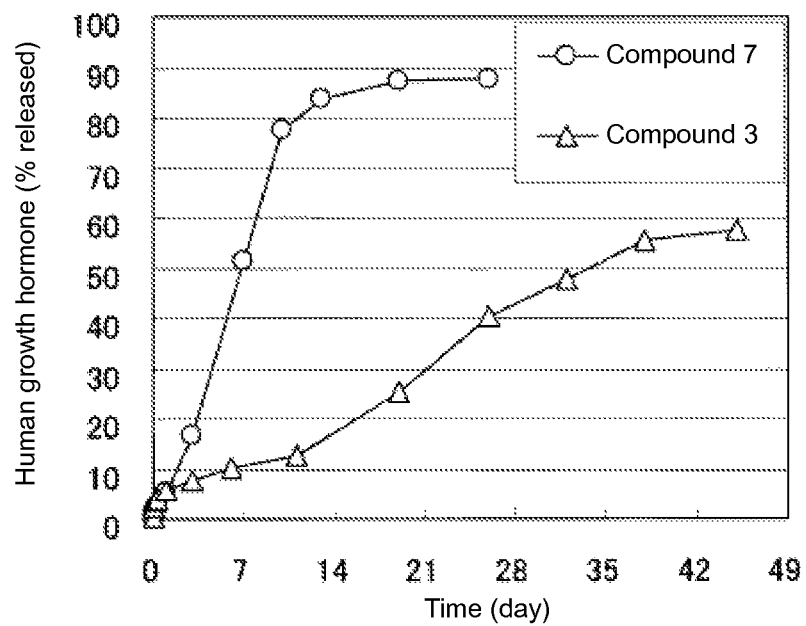
FIG. 1 shows drug release from microparticles encapsulating human growth hormone.

We form a microparticle by agglomeration of hydrophilic active substance containing particles which particle comprises an amphiphilic polymer and a hydrophilic active substance. The agglomeration is bonding of two or more particles by way of inter-particle force or other substance, and forming of a set. The inter-particle force is not specified particularly, but usable examples include hydrophobic interaction, hydrogen bond, and van der Waals force. The agglomeration is not limited to a state of mutual contact of particles, but substances having an affinity for particles may be present among particles, or particles may distribute in a matrix. As the substances having affinity for particles or the matrix, a polymer is preferred. By agglomeration of the hydrophilic active substance containing particles, as compared with a single particle, the effect that the encapsulation efficiency of the hydrophilic active substance is higher is attained. The particle diameter of the hydrophilic active substance containing particles to be associated is variable.

Microparticles are particles having the particle diameter ranging from sub-microns to sub-millimeters. The average particle diameter of microparticles is not particularly limited, but in the case of administration of the microparticles by injection to the human body, the greater the average particle diameter, the larger is the syringe needle, and the patient's burden is increased, and therefore from the viewpoint of lowering of the patient's burden, it is preferred to be in a range of 1 μm to 50 μm. The average particle diameter of microparticles may be determined by image analysis by using a scanning electron microscope.

The number of agglomerations of hydrophilic active substance containing particles for composing a microparticle is preferred to be in a range from 10 to the seventh power of 10, more preferably in a range from the fifth power of 10 to the seventh power of 10. The number of agglomerations is calculated from the average particle diameter of hydrophilic active substance containing particles and the average particle diameter of microparticles.

The amphiphilic polymer is composed of a hydrophobic segment of poly(hydroxy acid) and a hydrophilic segment of polysaccharides or polyethylene glycol. The amphiphilic property is a state having both hydrophilic and hydrophobic properties, and as for the hydrophilic property, when solubility in water is higher in a certain segment than in other segments, such segment is said to be hydrophilic. A hydrophilic segment is preferred to be soluble in water, but if hardly soluble, it is hydrophilic if solubility in water is higher than other segments. A certain segment is said to be hydrophobic if solubility in water is lower than other parts. A hydrophobic segment is preferred to be insoluble in water, but if soluble, it can be hydrophobic if solubility in water is lower than other segments.

Specific examples of poly(hydroxy acid) of the amphiphilic polymer include polyglycolic acid, polylactic acid, poly(2-hydroxy butyric acid), poly(2-hydroxy valeric acid), poly(2-hydroxy caproic acid), poly(2-hydroxy capric acid), poly(malic acid), and derivatives and copolymers of these high molecular compounds. However, since microparticles are desired to have no significant effects at the time of administration in human body, the poly(hydroxy acid) of amphiphilic polymer is also preferred to be a biocompatible high polymer. The biocompatible high polymer is a substance not having significant effects on the human body when administered, and more specifically the LD50 is preferred to be 2,000 mg/kg or more by oral administration of the high polymer in rat.

As poly(hydroxy acid) of the biocompatible high polymer, a copolymer of polylactic acid, and polyglycolic acid, or poly(lactic acid-glycolic acid) is preferred. When the poly (hydroxy acid) is a poly(lactic acid-glycolic acid), the composition ratio of the poly(lactic acid-glycolic acid) (lactic acid/glycolic acid) (mol/mol %) is not particularly limited, but the ratio is preferably 10/0 to 30/70, or more preferably 60/40 to 40/60.

When the hydrophilic segment of the amphiphilic polymer is polysaccharides, examples of the polysaccharides may include cellulose, chitin, chitosan, gellan gum, alginic acid, hyaluronic acid, pullulan, or dextran, and dextran is most preferable.

The amphiphilic polymer is preferably composed by graft polymerization of graft chain(s) of poly(hydroxy acid) in a main chain of polysaccharide. The average molecular weight of the main chain of polysaccharide is preferably 1,000 to 100,000, or more preferably 2,000 to 50,000, and the average molecular weight of the poly(hydroxy acid) is preferably 500 to 100,000, or more preferably 1,000 to 10,000. The value of average molecular weight of poly(hydroxy acid) to the average molecular weight of polysaccharides is preferably 0.01 times to 100 times, more preferably 0.02 times to 10 times, or most preferably 0.02 times to 1 times.

The number of graft chains of poly(hydroxy acid) bonded with the main chain of polysaccharides is preferably 2 to 50. The number of graft chains may be determined from the average molecular weight of graft type amphiphilic polymer, main chain of polysaccharides, and graft chain of poly(hydroxy acid).

When the hydrophilic segment of the amphiphilic polymer is polyethylene glycol, the amphiphilic polymer is preferred to be a block polymer of polyethylene glycol and poly(hydroxy acid). The term "block" refers to a portion segment of a polymer molecule, consisting of at least five or more monomer units, and being different in chemical structure or configuration between a portion segment and other adjacent portion segment, and a polymer formed of two or more blocks coupled straightly is called a block polymer. Each block forming a block polymer may comprise two or more monomer units, that is, a random, alternating, or gradient polymer may be formed. When the hydrophilic segment of the amphiphilic polymer is polyethylene glycol, the amphiphilic polymer is preferred to be a block polymer coupling one each of polyethylene glycol and polyhydroxy acid.

When the hydrophilic segment of the amphiphilic polymer is polyethylene glycol, specific examples of the polyethylene glycol to be used include straight-chain or branched polyethylene glycol or its derivatives, and a preferred example of polyethylene glycol derivative is polyethylene glycol monoalkyl ether. The alkyl group of the polyethylene glycol monoalkyl ether is a straight-chain or branched alkyl group having 1 to 10 carbon atom(s), and a branched alkyl group having 1 to 4 carbon atom(s) is more preferable, and methyl, ethyl, propyl, and iso-propyl groups are particularly desired.

The average molecular weight of the polyethylene glycol is not particularly limited, but is preferably 2,000 to 15,000, more preferably 2,000 to 12,000, even more preferably 4,000 to 12,000, and particularly preferably 5,000 to 12,000.

When the hydrophilic segment of the amphiphilic polymer is polyethylene glycol, the average molecular weight of the poly(hydroxy acid) is not particularly limited, but is preferably 5,000 to 200,000, more preferably 15,000 to 150,000, or even more preferably 20,000 to 100,000. The value of average molecular weight of poly(hydroxy acid) to the average molecular weight of polyethylene glycol is preferably 1.0 times or more, more preferably 2 times or more, most preferably 4 times or more, and particularly preferably 4 times or more to 25 times or less.

The average molecular weight refers to the number-average molecular weight unless otherwise specified, and the number-average molecular weight is an average molecular weight calculated by a method not considering weighting of magnitude of a molecule, and the average molecular weight of amphiphilic polymer, polysaccharides, and polyethylene glycol can be obtained as the molecular weight converted into polystyrene or pullulan measured by gel permeation chromatography (GPC). The average molecular weight of poly(hydroxy acid) can be determined from the ratio of peak integral value of terminal residue and peak integral value of others than terminal residue as measured by nuclear magnetic resonance ($^1$H-NMR) measurement.

The amphiphilic polymer composed of polysaccharides and poly(hydroxy acid) may be synthesized by any known method and, as far as a reversed-phase emulsion can be formed, the synthesizing method is not specified, and it can be manufactured, for example, in any one of the following methods (1), (2), and (3):

1) In the presence of a tin catalyst, a hydroxy acid activating monomer is added to polysaccharides to carry out a polymerization reaction, and poly(hydroxy acid) is further added, and a graft type amphiphilic polymer is manufactured (Macromolecules, 31, 1032-1039 (1998)).
2) The hydroxyl group of partially non-protected polysaccharides of which majority of hydroxy group is protected by a substituent is activated by a base, a hydroxy acid activating monomer is added to form graft chain(s) composed of poly(hydroxy acid), and finally the protective group is removed, and a graft type amphiphilic polymer is manufactured (Polymer, 44, 3927-3933, (2003)).
3) In polysaccharides, a copolymer of poly(hydroxy acid) is added to execute condensation reaction by using a dehydrating agent and/or a functional activating agent, and a graft type amphiphilic polymer is manufactured (Macromolecules, 33, 3680-3685 (2000)).

The amphiphilic polymer composed of polyethylene glycol and poly(hydroxy acid) may be synthesized by any known method and, as far as a reversed-phase emulsion can be formed, the synthesizing method is not specified and, for example, in the presence of a tin catalyst, a hydroxy acid activating monomer is added to polyethylene glycol to carry out a polymerization reaction to form poly(hydroxy acid), and an amphiphilic block polymer is manufactured (Journal of Controlled Release, 71, 203-211 (2001)).

The structure of the hydrophilic active substance containing particle comprising the amphiphilic polymer and hydrophilic bioactive substance is not particularly limited, but as far as the hydrophilic active substance containing particle has a hydrophilic segment of an amphiphilic polymer in the inside, and has an outer layer of a hydrophobic segment of an amphiphilic polymer, it is preferable because the contained hydrophilic active substance can be maintained more stably.

When the hydrophilic active substance containing particle is a particle having a hydrophilic segment of an amphiphilic polymer in the inside, and having an outer layer of a hydrophobic segment of an amphiphilic polymer, it is one of the preferred embodiments if a surface modifier is bonded to the outer layer of poly(hydroxy acid). Bonding may be either non-covalent bonding or covalent bonding. Non-covalent bonding is preferably hydrophobic interaction, but may include electrostatic interaction, hydrogen bond, or van der Waals force, or a combination thereof. In non-covalent bonding, the hydrophobic outer layer of fine particles containing the amphiphilic polymer, and the hydrophobic portion of a surface modifier described below may be preferably bonded to each other by hydrophobic interaction. In this case, the dispersant of fine particles is particularly preferred to be water, buffer solution, physiological saline, surface modifier aqueous solution, or fine particle dispersant of hydrophilic solvent.

The surface modifier is preferably a compound capable of stabilizing the water-oil interface of S/O/W type emulsion, or the oil-oil emulsion interface of S/O1/O2 type emulsion, and more preferably a compound having properties for enhancing the colloid stability of microparticles. The surface modifier may be one type or a mixture of plural types. The property of enhancing the colloid stability means to prevent or delay aggregation of microparticles in the solvent.

The surface modifier is preferred to be an amphiphilic compound or a hydrophilic polymer.

The hydrophilic polymer of the surface modifier is preferably any one selected from the group consisting of polyethylene glycol, polyvinyl pyrrolidone, polyvinyl alcohol, polyethylene imine, polyacrylic acid, polymethacrylic acid, poly-1,3-dioxolane, 2-methacryloyl oxyethyl phosphoryl choline polymer, poly-1,3,6-trioxane, polyamino acid, peptide, protein, saccharides, and analogs thereof.

Analogs of the hydrophilic polymer may include a surfactant having a hydrophilic polymer partially modified by a hydrophobic group such as a long-chain alkyl, but are not particularly limited to this.

As a polyethylene glycol analog of a surface modifier, it is preferred to use Pluronic (registered trademark) commercially available by BASF or its equivalents.

As a polyamino acid of a surface modifier, polyaspartic acid, polyglutamic acid, or their analogs may be preferably used. An analog introducing a long-chain alkyl group in part of polyaspartic acid or polyglutamic acid is particularly preferable.

As a peptide of a surface modifier, a basic peptide may be used.

As a protein of a surface modifier, gelatin, casein, or albumin is preferred for enhancing the dispersion performance of particles. As a protein, an antibody is one of preferred examples.

As saccharides of a surface modifier, monosaccharides, oligosaccharides, and polysaccharides are preferable. As polysaccharides, cellulose, chitin, chitosan, gellan gum, alginic acid, hyaluronic acid, pullulan, and dextran are preferable. Particularly, cholesteryl pullulan is preferable in view of better dispersibility of particles. Analogs of any one selected from the group consisting of cellulose, chitin, chitosan, gellan gum, alginic acid, hyaluronic acid, pullulan, and dextran are preferable.

As the surface modifier, these examples of peptide, protein, and saccharides are particularly preferred to be analogs partly modifying the hydrophobic group of a long-chain alkyl, or analogs modifying the hydrophilic polymer or the amphiphilic compound.

In the surface modifier, the amphiphilic compound includes a lipid as one of the preferred examples.

In the surface modifier, the amphiphilic compound includes a surfactant as one of the preferred examples. Preferred examples of the surfactant include: nonionic active agents such as polyoxyethylene-polypropylene glycol copolymer, sucrose fatty acid ester, polyethylene glycol fatty acid ester, polyoxyethylene sorbitan mono-fatty acid ester, polyoxyethylene sorbitan di-fatty acid ester, polyoxyethylene glycerin mono-fatty acid ester, polyoxyethylene glycerin di-fatty acid ester, polyglycerin fatty acid, polyoxyethylene castor oil, polyoxyethylene hardened castor oil; alkyl sulfates such as lauryl sodium sulfate, lauryl ammonium sulfate, stearyl sodium sulfate; or lecithin.

The hydrophilic active substance is exemplified by low molecular compound, protein, peptide, DNA, RNA, or modifying nucleic acid. Even a hydrophobic drugs may be contained in the microparticle if made hydrophilic by using a solubilizing agent. The solubilizing agent herein preferably includes cyclodextrin and its analogs.

The protein or the peptide used as the hydrophilic active substance is not particularly limited, but a bioactive protein or a bioactive peptide is preferred. The bioactive protein or the bioactive peptide include peptide hormone, cytokine, enzyme protein, or antibody. Specific examples include: GLP-1 receptor antagonist peptide such as Exendin-4, parathyroid hormone (PTH), calcitonin, insulin, insulin-like growth factor, angiotensin, glucagon, GLP-1; bombesin, motilin, gastrin, growth hormone, prolactin (luteotropic hormone), gonadotropin (gonadotropic hormone), thyrotropic hormone, adrenocorticotropic hormone (ACTH), ACTH derivative (ebiratide), melanocyte stimulating hormone, follicle stimulating hormone (FSH), sermorelin, vasopressin, oxytocin, protirelin, luteinizing hormone (LH), corticotropin, secretin, somatropin, thyrotropin (thyroid stimulating hormone), stomatostatin, gonadotropin releasing hormone (GnRH), G-CSF, erythropoetin (EPO), thrombopoetin (TPO), megakaryocyte potentiator, HGF, EGF, VEGF, interferon α, interferon β, interferon γ, interleukins, FGF (fibroblast growth factor), BMP (bone marrow proteins), thymic humor factor (THF), serum thymic factor (FTS), superoxide dimustase (SOD), urokinase, lisozyme, tissue plasminogen activator, asparakinase, kallikrein, Ghrelin, adiponectin, leptin, atrial sodium diuretic peptide, atrial sodium diuretic factor, cerebral sodium diuretic peptide (BNP), conantokin G, dynorphin, endorphin, Kyotorphin, enkephalin, neurotensin, angiostin, bradykinin, substance P, kalidin, hemoglobin, protein C, VIIa factor, glycocerebrosidase, streptokinase, staphylokinase, thymosin, pancreozimine, cholecistokinin, human placenta lactogen, tumor necrosis factor (TNF), polymixin B, cholistine, gramicidin, bacitracin, thymopoetin, bombecin, cerulein, thymostimulin, secretin, resistin, hepcidin, neuropetide Y, neuropeptide S, cholecistokinine-pancreozimine (CCK-PZ), brain-derived nutrient factor (BDNF), vaccine, and the like. These bioactive proteins or bioactive peptides may be natural proteins or peptides, or derivatives modified in part of their sequence, or compounds modified by polyethylene glycol or sugar chain.

When the hydrophilic active substance is DNA, RNA, or modifying nucleic acid, it may be any one of cationic surfactant, cationic lipid, cationic polymer, or other compounds complexed with the analogs thereof.

Saccharides used as the hydrophilic active substance include hyaluronic acid, heparin, dextran sulfate, dextran or FITC labeled dextran (for example, FD40, etc.).

We also provide a method for manufacturing the microparticle formed by agglomeration of the hydrophilic active substance containing particles, the method comprising:

a) a step of forming a reversed-phase emulsion by mixing an aqueous solvent containing the hydrophilic active substance and a water-immiscible organic solvent dissolving the amphiphilic polymer, b) a step of obtaining a solid content containing the hydrophilic active substance by removing the solvent from the reversed-phase emulsion, and c) a step of introducing the solid content or a dispersion liquid containing the solid content into a liquid phase containing the surface modifier.

In the method for manufacturing the microparticle formed by agglomeration of the hydrophilic active substance containing particles, the reversed-phase emulsion is formed by adding an aqueous solvent containing the hydrophilic active substance to a water-immiscible organic solvent dissolving an amphiphilic polymer and mixing them. If necessary, it is possible to use, for example, an agitating device such as magnetic stirrer, a turbine agitating device, a homogenizer, or a membrane emulsifying device provided with a porous film. The water-immiscible organic solvent is an organic solvent of which solubility in water is 30 g (water-immiscible organic solvent)/100 ml (water) or less, and other organic solvents of which solubility in water is higher than the specified value are characterized as water-miscible organic solvents.

As the aqueous solution at step (a), water or water solution containing a water-soluble substance is used. The water-soluble substance may be any one of inorganic salts, saccharides, organic salts, amino acid, and the like.

The property of water immiscible organic solvent at step (a) is not particularly limited, but it is preferably a solvent capable of dissolving poly(hydroxyl acid) as the hydrophobic segment of the amphiphilic polymer, and hardly dissolving or not dissolving the hydrophilic segment. The water-immiscible organic solvent is preferred to be dissipated and removed by freeze-drying or the like, and is preferred to be 0.1 g (water-immiscible organic solvent)/100 ml (water) or less. Specific examples of the water-immiscible organic solvent include ethyl acetate, isopropyl acetate, butyl acetate, dimethyl carbonate, diethyl carbonate, methylene chloride, and chloroform. The ratio of the water-immiscible organic solvent to the aqueous solvent is preferably 1,000:1 to 1:1, more preferably 100:3 to 3:1. The concentration of the amphiphilic polymer in the water-immiscible organic solvent varies with the type of the water immiscible organic solvent or the amphiphilic polymer, but is preferably 0.01 to 90% (w/w), more preferably 0.1 to 50% (w/w), or even more preferably 1 to 20% (w/w).

At step (a), in the process of forming a reversed-phase emulsion by the aqueous solvent containing the hydrophilic active substance and the water-immiscible organic solvent dissolving the amphiphilic polymer, depending on the pharmacological purpose, a reversed-phase emulsion may be formed by using a water-immiscible organic solvent dissolving two or more types of amphiphilic polymer.

At step (a), in the process of forming a reversed-phase emulsion by the aqueous solvent containing the hydrophilic active substance and the water-immiscible organic solvent dissolving the amphiphilic polymer, to assist formation of the reversed-phase emulsion and to form a uniform and fine reversed-phase emulsion, an assisting agent may be added. Such assisting agent may be preferably a compound selected from the group consisting of alkyl alcohol having 3 to 6 carbon atoms, alkyl amine having 3 to 6 carbon atoms, and alkyl carboxylic acid having 3 to 6 carbon atoms. The structure of alkyl chain of these assisting agents is not specified particularly, and either straight-chain structure or branched structure may be applicable, or saturated alkyl or non-saturated alkyl may be usable. In particular, tert-butanol, isobutanol, and pentanol are preferred as the assisting agent.

The average particle diameter of the reversed-phase emulsion at step (a) is variable with the particle diameter of the desired microparticle, and is not particularly limited, but to manufacture a microparticle for a pharmaceutical preparation which is one of the applications of the microparticle, the upper limit of the average particle diameter is preferably 50 μm, more preferably 5 μm, even more preferably 500 nm, particularly preferably 150 nm, and most preferably 100 nm. The lower limit of the average particle diameter of the reversed-phase emulsion is preferably 10 nm, or more preferably 50 nm.

Next, in the manufacturing method of a microparticle, it is important to include step (b) of obtaining a solid content containing the hydrophilic active substance by removing the solvent from the reversed-phase emulsion obtained at step (a).

At step (b), the method of removing the solvent from the reversed-phase emulsion is not particularly limited, but may include, for example, heating, in-vacuo drying, dialysis, freeze-drying, centrifugal operation, filtration, re-sedimentation, and a combination thereof.

Among these methods of removing the solvent from the reversed-phase emulsion, freeze-drying is particularly preferred because it is small in structural changes due to uniting of particles in the reversed-phase emulsion, and is capable of avoiding degeneration due to high temperature of the hydrophilic active substance. The condition and the apparatus of freeze-drying include a freezing process and a drying process at reduced pressure, and the process is particularly preferred to consist of preliminary freezing step as an ordinary method of freeze-drying, a primary drying step at reduced pressure and low temperature, and a secondary drying step at reduced pressure. For example, by cooling and freezing below the melting point of aqueous solution and water immiscible organic solvent, for composing a reversed-phase emulsion, and then drying at reduced pressure, a freeze-dried hydrophilic active substance containing solid content is obtained. The temperature of preliminary freezing may be determined properly by experiment considering from the solvent composition, and is generally preferred to be −20° C. or less. The degree of reduced pressure in the drying process may be determined properly by experiment considering from the solvent composition, and is generally preferred to be 3,000 Pa or less, or more preferably 500 Pa or less, for shortening of the drying time. For freeze-drying, it is preferred to employ a freeze-drying apparatus for laboratory having a cold trap and connectable to a vacuum pump, or a rack type vacuum freeze-drying apparatus used in manufacture of pharmaceutical preparations, and after preliminary freezing by using liquid nitrogen or refrigerant, drying at reduced pressure is executed at cooled temperature or room temperature by using a vacuum pump or other pressure reducing device.

The solid content containing the hydrophilic active substance obtained at step (b) is obtained as an aggregate of hydrophilic active substance containing particles comprising the amphiphilic polymer, which aggregate conforms to the structure of the reversed-phase emulsion. The aggregate is an irregular mass gathering fine particles by inter-particle force, and is clearly distinguished in shape from the microparticle. The average particle diameter of the hydrophilic active substance containing fine particles for forming this aggregate is variable with the particle diameter of the desired microparticle, and is not particularly limited, but to manufacture a microparticle for a pharmaceutical preparation which is one of the applications of the microparticle, the upper limit of the average particle diameter is preferably 50 μm, more preferably 5 μm, most preferably 500 nm, especially 150 nm, particularly 100 nm. The lower limit of the average particle diameter of the hydrophilic active substance containing fine particles is preferably 10 nm, or more preferably 50 nm.

In the method for manufacturing the microparticle, it is important to include step (c) of introducing the solid content containing the hydrophilic active substance or a dispersion liquid containing the solid content in a liquid phase containing the surface modifier.

At step (c), the method of introducing the solid content or the dispersion liquid containing the solid content in a liquid phase containing the surface modifier includes, for example, a method of adding the solid content in a liquid phase containing the surface modifier, and a method of dispersing the solid content once in a dispersion medium, and adding the obtained dispersion liquid (solid-in-oil (S/O) suspension) in a liquid phase containing the surface modifier.

When dispersing the solid content containing the hydrophilic active substance once in a dispersion medium, the dispersion medium is not particularly limited, but is preferably a solvent capable of dissolving poly(hydroxy acid), but not dissolving substantially the hydrophilic segment composing the amphiphilic polymer, for the purpose of sustaining the hydrophilic active substance containing particle structure composed of the amphiphilic polymer having the structure of the reversed-phase emulsion for composing the hydrophilic active substance containing solid content. The solvent capable of dissolving poly(hydroxy acid), but not dissolving substantially the hydrophilic segment is a solvent of which solubility of hydrophilic segment in the solvent is 50 mg/mL or less, preferably 10 mg/mL or less.

The dispersion medium may be either water-immiscible organic solvent or water miscible organic solvent as far as having the features mentioned above, and the water-immiscible organic solvent is more preferable. Specific examples of the water-immiscible organic solvent capable of dissolving poly(hydroxy acid) of amphiphilic polymer, but not dissolving substantially in the hydrophilic segment include ethyl acetate, isopropyl acetate, butyl acetate, dimethyl carbonate, diethyl carbonate, methylene chloride, chloroform, dioxane, toluene, and xylene.

The dispersion medium for dispersing the solid content containing the hydrophilic active substance may contain various additives soluble in the dispersion medium, for the purpose of controlling the releasing speed of the hydrophilic active substance due to decomposition or disintegration of the hydrophilic active substance containing particles, for example, an acidic compound, a basic compound, an amphiphilic polymer, or a biodegradable polymer.

The liquid phase at step (c) is preferably capable of dissolving the surface modifier, and is higher in boiling point than the hydrophilic active substance containing solid content dispersion medium, and may include any one of aqueous solvent, water-immiscible organic solvent, and water miscible organic solvent. The aqueous solvent is water, or water solution containing a water soluble component, and the water soluble component includes, or example, inorganic salts, saccharides, organic salts, and amino acids; the water-immiscible organic solvent includes, for example, silicone oil, sesame oil, soybean oil, corn oil, cotton seed oil, coconut oil, linseed oil, mineral oil, castor oil, hardened castor oil, liquid paraffin, n-hexane, n-heptane, glycerol, and oleic oil; and the water miscible organic solvent includes, for example, glycerin, acetone, ethanol, acetic acid, dipropylene glycol, triethanol amine, and triethylene glycol. The liquid phase at step (c) is preferably an aqueous solvent or a water miscible organic solvent. When the liquid phase is an aqueous solvent, and the dispersion medium is a water-immiscible organic solvent, the suspension obtained at step (c) is a so-called solid-in-oil-water (S/O/W) type emulsion, and when the liquid phase is water-immiscible organic solvent or water miscible organic solvent, and is not miscible in the dispersion medium, it is a solid-in-oil-in-oil (S/O1/O2) type emulsion.

The ratio by volume of the liquid phase to the dispersion medium for dispersing the hydrophilic active substance containing solid content is generally 1,000:1 to 1:1,000, or preferably 100:1 to 1:100.

The concentration of the surface modifier in the liquid phase is variable with the type of the surface modifier, and is preferably 0.01 to 90% (w/v), more preferably 0.1 to 50% (w/v), or even more preferably 5 to 10% (w/v).

The surface modifier may be bonded to a poly(hydroxy acid) outer layer of the amphiphilic polymer of the microparticle, and the bonding amount in this case is preferably 0.0001% to 1% of the weight of the microparticle.

In the liquid phase at step (c), in addition to the surface modifier, various additives may be added depending on the pharmacological purpose, such as buffer agent, antioxidant, salt, polymer, or sugar.

At step (c), it is also preferred to add inorganic salts in the liquid phase. Inorganic salts are preferred to be alkaline metal salt or alkaline earth metal salt, and sodium chloride is particularly preferable. The concentration of inorganic salts in the liquid phase is preferably 0 to 1 M, more preferably 10 mM to 1 M, or even more preferably 10 mM to 100 mM.

At step (c), to manufacture a microparticle of a smaller particle size, the formed solid-in-oil-in-water (S/O/W) type emulsion or solid-in-oil-in-oil (S/O1/O2) type emulsion may be processed by an emulsifying operation. The emulsifying method is not particularly limited as far as a stable emulsion can be manufactured. For example, the method includes an agitating method, or a method by using a high-pressure homogenizer, or a high-speed homo-mixer.

At step (c), when the dispersion liquid obtained by dispersing the solid content containing the hydrophilic active substance once in the dispersion medium is added in the liquid phase containing the surface modifier, by removing the dispersion medium, a desired suspension of the microparticle formed by agglomeration of the hydrophilic active substance containing particles is obtained. The method of removing the dispersion medium is not particularly limited, but may include methods of drying in liquid, dialysis, freeze-drying, centrifugal operation, filtration, and re-sedimentation, and drying in liquid or freeze-drying may be particularly preferred. At step (c), when an aqueous solvent is used as the liquid phase, an aqueous dispersant of the microparticle is obtained in this process.

By removing the liquid phase from the microparticle dispersant obtained in this process, the microparticle can be obtained. The method of removing the liquid phase is not particularly limited, but may preferably include methods of distilling-away by evaporation, dialysis, freeze-drying, centrifugal operation, and filtration.

Fields of application of the microparticle are wide, and versatile, and it is particularly used as a pharmaceutical preparation. When the microparticle is used as the pharmaceutical preparation, aside from microparticles, various pharmacological useful additives may be contained, and usable additives include buffer agent, antioxidant, salt, polymer, or sugar.

When the microparticle is used as a pharmaceutical preparation, the method of administration includes, for example, oral administration and parental administration, and the parental administration is preferred. The parental administration includes hypodermic administration, intramuscular administration, enteric administration, pulmonary administration, local administration (nose, skin, eye), and body cavity administration, and the hypodermic and intramuscular injections are preferred in particular. The dose and the number of times of administration of the pharmaceutical preparation in the body of the patient may be properly selected depending on the hydrophilic active substance, route of administration, age and body weight of the patient, or severity of the symptom, but usually a dose of 0.1 μg to 100 mg, preferably 1 μg to 10 mg is administered per day per adult person.

EXAMPLES

Examples are shown below, but this disclosure is not limited to the examples described herein.

Example 1

Synthesis of dextran-polylactic Acid (PLA)

1.1 Synthesis of TMS-dextran (compound 1)

Dextran (NACALAI TESQUE, INC. NAKARAI standard special grade conforming product, number-average molecular weight: 13000, 5.0 g) was added to formamide (100 ml), and heated to 80° C. In this solution, 1,1,1,3,3,3-hexamethyldisilazane (100 ml) was added by dropping for 20 minutes. After dropping, the solution was stirred for 2 hours at 80° C. After completion of the reaction, the reaction solution was returned to room temperature, and the solution was separated into two layers by a dispensing funnel. The upper layer was concentrated at reduced pressure, and methanol (300 ml) was added, and the obtained solid content was filtered and dried, and TMS-dextran (11.4 g) was obtained as white solid content.

1.2 Synthesis of TMS-dextran-PLA (compound 2)

Compound 1 (0.5 g) and tert-butoxy potassium (35 mg) were dried for 1 hour at reduced pressure, and tetrahydrofurane (20 ml) was added, and the mixture was stirred for 1 hour at room temperature. In this solution, tetrahydrofurane (20 ml) solution of (L)-lactide (4.49 g) was dropped, and the mixture was stirred for 5 minutes. After completion of reaction, the solvent was concentrated at reduced pressure, and purified by reprecipitation by a chloroform-methanol system, and TMS-dextran-PLA (1.9 g) was obtained as white solid content.

1.3 Synthesis of dextran-PLA (compound 3)

In chloroform (24 ml) solution of compound 2 (1.9 g), methanol (10.8 ml) and 12N hydrochloric acid (1.2 ml) were added, and stirred for 30 minutes at room temperature. The solvent was distilled away at reduced pressure, and the residue was dissolved in chloroform (10 ml), and dropped into diethyl ether cooled to 0° C., and the product was deposited. The deposition matter was filtered away, and concentrated at reduced pressure, and dextran-PLA (1.6 g) was obtained. The weight-average molecular weight of this polymer was 48720, and the number-average molecular weight was 43530. (Measurement by GPC: column Toso TSK-gel α-5000×2, DMF system solvent, detector RI, standard product, pullulan). The average molecular weight of the graft chain of this polymer determined by $^1$H-NMR measurement was 2300. The number of graft chains was 10 to 12.

Example 2

Synthesis of dextran-poly(lactic acid-glycolic acid) (PLGA)

2.1 Synthesis of TMS-dextran-PLGA (compound 4, compound 5, compound 6)

Compound 1 (0.5 g) and tert-butoxy potassium (35 mg) were dried for 1 hour at reduced pressure, and tetrahydrofurane (10 ml) was added, and the mixture was stirred for 1 hour at room temperature. In this solution, tetrahydrofurane (15 ml) solution of (DL)-lactide (1.12 g) and glycolide (0.9 g) was dropped, and the mixture was stirred for 5 minutes. After completion of reaction, the solvent was concentrated at reduced pressure, and purified by reprecipitation by a chloroform-methanol system, and TMS-dextran-PLGA (1.96 g) was obtained as white solid content (compound 4). In the same manner, by the charging amount of (DL)-lactide (0.784 g) and glycolide (0.63 g), compound 5 was synthesized, and by the charging amount of (DL)-lactide (1.12 g) and glycolide (0.9 g), compound 6 was synthesized.

2.2 Synthesis of dextran-PLGA (compound 7, compound 8, compound 9)

In chloroform (14 ml) solution of compound 4 (1.96 g), methanol (6.3 ml) and 12N hydrochloric acid (0.7 ml) were added, and stirred for 30 minutes at room temperature. The solvent was distilled away at reduced pressure, and the residue was dissolved in chloroform (10 ml), and dropped into diethyl ether cooled to 0° C., and the product was deposited. The deposition matter was filtered away, and concentrated at reduced pressure, and dextran-PLGA (1.25 g) was obtained (compound 7). From compounds 5 and 6, dextran-PLGA products were obtained as the same manner except that trifluoroacetic acid was used (compound 8, compound 9). The weight-average molecular weight and the number-average molecular weight of the polymer of compounds 7 to 9 were determined by GPC measurement (column Toso TSK-gel α-5000×2, DMF system solvent, detector RI, standard product, pullulan). The average molecular weight of the graft chain and the number of graft chains were determined by $^1$H-NMR measurement.

As for compound 7, the weight-average molecular weight was 43,820, the number-average molecular weight was 33,422, the graft chain molecular weight was 1,900, and the number of graft chains was 7 to 10.

As for compound 8, the weight-average molecular weight was 94,088, the number-average molecular weight was 81,250, the graft chain molecular weight was 3,250, and the number of graft chains was 21.

As for compound 9, the weight-average molecular weight was 137,695, the number-average molecular weight was 109,630, the graft chain molecular weight was 6,442, and the number of graft chains was 15.

Example 3

Preparation Method of Microparticles Encapsulating Human Growth Hormone (hGH)

5 mg of dextran-polylactic acid (PLA) of Example 1 (average molecular weight of dextran is 13,000, average molecular weight of PLA is 2,300, number of graft chains of PLA is 10 to 12, compound 3) or dextran-poly(lactic acid-glycolic acid) (PLGA) of Example 2 (average molecular weight of dextran:

13,000, average molecular weight of PLGA is 19,000, number of graft chains of PLGA 7 to 10, compound 7) was dissolved in 100 µl of dimethyl carbonate to prepare a polymer solution of 50 mg/ml. In this polymer solution, 20 µl of tert-butanol was added, and 20 µl of 2 mg/ml hGH aqueous solution was dropped, and stirred by vortex to prepare a reversed-phase emulsion. This reversed-phase emulsion was frozen preliminarily, and was freeze-dried by using a freeze-drying apparatus (EYELA, FREEZE DRYER FD-1000), at trap cooling temperature of −45° C., and degree of vacuum of 20 Pa, for 24 hours. The obtained solid content was dispersed in 200 µl of dimethyl carbonate to prepare an S/O suspension. This S/O suspension was dropped in 2 ml of aqueous solution containing 10% Pluronic F-68 (a registered trademark of BASF), and was stirred and emulsified in a vortex mixer to prepare S/O/W type emulsion. From this S/O/W type emulsion, the water-immiscible organic solvent was removed by drying in liquid, and a microparticle dispersion liquid was obtained. The microparticle dispersion liquid was preliminarily frozen by liquid nitrogen, and was freeze-dried by using a freeze-drying apparatus (EYELA, FREEZE DRYER FD-1000), at trap cooling temperature of −45° C., and degree of vacuum of 20 Pa, for 24 hours, and hGH-encapsulating microparticle powder was obtained. The obtained microparticles were observed by a scanning electron microscope (SEM: HITACHI, S-4800), and the average particle diameter was calculated, and the average particle diameter of the microparticles was 4.0 µm.

Example 4

Measurement of Drug Encapsulation Efficiency of Microparticles Encapsulating Human Growth Hormone (hGH)

20 mg of microparticles encapsulating human growth hormone prepared in the method of Example 3 by using dextran-PLA (compound 3) or dextran-PLGA (compound 7) polymer was weighed by using a 1.5 ml Eppendorf tube, and was dissolved in 1 ml of buffer solution A (PBS containing 0.1% bovine serum albumin, 0.1% Pluronic F-68 (a registered trademark of BASF), and 0.02% sodium azide), and was centrifuged for 10 minutes at 18,000×g, and was separated into particles (precipitation) and a supernatant. The supernatant was collected in other tube, and the particles were suspended again in 1 ml of buffer solution, and the centrifugal operation and the separation into particles and a supernatant were conducted again in the same conditions. This cleaning operation was repeated once more (total three times of centrifugal operation), and the human growth hormone concentration of each supernatant collected by the centrifugal operations was measured by using an ELISA kit (manufactured by R&D Systems). From the charged amount of hGH at the time of preparation of particles (particle weight 20 mg), the hGH total amount of three supernatants by centrifugal operations was subtracted, and the encapsulation efficiency was calculated according to the formula below:

$$\text{Encapsulation efficiency (\%)} = \frac{(\text{charged } hGH \text{ amount (ng)} - hGH \text{ amount total in supernatants (ng)})}{\text{charged } hGH \text{ amount (ng)}} \times 100$$

In dextran-PLA microparticles or dextran-PLGA microparticles, the encapsulation efficiency of hGH was 92.6% in dextran-PLA microparticles, and 85.7% in dextran-PLGA microparticles, and it was proved that the protein drug can be encapsulated at a high efficiency in both particles.

Example 5

Analysis of In-Vitro Drug Release Speed from Microparticles Encapsulating Human Growth Hormone (hGH)

The microparticles centrifuged three times in Example 4 were suspended and dispersed in 1.2 ml of buffer solution A. From this solution, a part (40 µl) was transferred into other tube, and was centrifuged for 10 minutes at 18,000×g to precipitate the particles, and 30 µl of supernatant was collected in a different tube (0-hour sample). The remaining particle suspension was put in a 1.5 ml Eppendorf tube, and was rolled and mixed slowly in an incubator at 37° C., by using a rotator at a speed of 6 rpm. From this solution, a small portion (40 µl) was dispensed at specific time intervals, and the supernatant was separated similarly by centrifugal operation. In the supernatant sample collected at each time, the hGH concentration was measured by using the ELISA kit, and the release amount (%) was calculated in the formula below:

$$\text{Release amount (\%)} = \frac{(hGH \text{ concentration in supernatant (ng/ml)} \times 1.2 \text{ (ml)})}{\text{encapsulated } hGH \text{ amount (ng) in 20 mg of particles}} \times 100$$

FIG. 1 shows time-course changes of drug release from microparticles manufactured by using dextran-PLA or dextran-PLGA polymer. In both particles, initial burst was hardly observed, and the drug was released linearly in proportion to the lapse of time, and a favorable profile was observed. The time required for 50% release of the drug was about 1 month in the dextran-PLA microparticle, and about 1 week in the dextran-PLGA microparticle, and it was suggested that the release speed can be controlled by selecting the type of poly (hydroxy acid).

Example 6

Preparation Method of Microparticles Encapsulating Human Insulin 5 mg of dextran-PLA (average molecular weight of dextran is 13,000, average molecular weight of PLA is 2,300, number of graft chains of PLA is 10 to 12, compound 3) or dextran-PLGA (average molecular weight of dextran is 13,000, average molecular weight of PLGA is 19,000, number of graft chains of PLGA 7 to 10, compound 7) was dissolved in 100 µl of dimethyl carbonate to prepare a polymer solution of 50 mg/ml. In this polymer solution, 20 µl of tert-butanol was added, and 20 µl of 2 mg/ml human insulin aqueous solution was dropped, and stirred by vortex to prepare a reversed-phase emulsion. This reversed-phase emulsion was frozen preliminarily by liquid nitrogen, and was freeze-dried by using a freeze-drying apparatus (EYELA, FREEZE DRYER FD-1000), at trap cooling temperature of −45° C., and degree of vacuum of 20 Pa, for 24 hours. The obtained solid content was dispersed in 200 µl of dimethyl carbonate to prepare an S/O suspension. This S/O suspension was dropped in 2 ml of aqueous solution containing 10% Pluronic F-68 (a registered trademark of BASF), and was stirred and emulsified in a vortex mixer to prepare an S/O/W type emulsion. From this S/O/W type emulsion, the water-immiscible organic solvent was removed by drying in liquid, and a microparticle dispersion liquid was obtained. The microparticle dispersion liquid was preliminarily frozen by liquid nitrogen, and was freeze-dried by using a freeze-drying apparatus (EYELA, FREEZE DRYER FD-1000), at trap cooling temperature of −45° C., and degree of vacuum of 20 Pa, for 24 hours, and human insulin-encapsulating microparticle powder was obtained. The obtained microparticles were observed by a scanning electron microscope (SEM: HITACHI, S-4800), and the average particle diameter was calculated, and the average particle diameter was 6.4 μm in the microparticles obtained from compound 3, and 5.3 μm in the microparticles obtained from compound 7.

Example 7

Measurement of Drug Encapsulation Efficiency of Microparticles Encapsulating Human Insulin 20 mg of microparticles encapsulating human insulin prepared in the method of Example 6 by using dextran-PLGA (compound 7) polymer was weighed by using a 1.5 ml Eppendorf tube, and was dissolved in 1 ml of buffer solution A (PBS containing 0.1% bovine serum albumin, 0.1% Pluronic F-68 (a registered trademark of BASF), and 0.02% sodium azide), and was centrifuged for 10 minutes at 18,800×g, and was separated into particles (precipitation) and a supernatant. The supernatant was collected in other tube, and the particles were suspended again in 1 ml of buffer solution, and the centrifugal operation and the separation into particles and a supernatant were conducted again in the same conditions. This cleaning operation was repeated once more (total three times of centrifugal operation), and the human insulin concentration of each supernatant collected by the centrifugal operations was measured by sandwich ELISA method. From the charged amount of human insulin at the time of preparation of particles (per particle weight 20 mg), the human insulin total amount of three supernatants by centrifugal operations was subtracted, and the encapsulation efficiency was calculated according to the formula below:

$$\text{Encapsulation efficiency (\%)} = \frac{\text{(charged insulin amount (ng)} - \text{insulin amount total in supernatants (ng))}}{\text{charged insulin amount (ng)}} \times 100$$

In dextran-PLA microparticles or dextran-PLGA microparticles, the encapsulation efficiency of human insulin was 75.7%, and it was proved that the drug can be encapsulated at a high efficiency.

Example 8

Analysis of In-Vitro Drug Release Speed from Microparticles Encapsulating Human Insulin The microparticles centrifuged three times in Example 7 were suspended and dispersed in 1.2 ml of buffer solution A. From this solution, a part (40 μl) was transferred into other tube, and was centrifuged for 10 minutes at 18,800×g to precipitate the particles, and 30 μl of supernatant was collected in a different tube (0-hour sample). The remaining particle suspension was put in a 1.5 ml Eppendorf tube, and was rolled and mixed slowly in an incubator at 37° C., by using a rotator at a speed of 6 rpm. From this solution, a small portion (40 μl) was dispensed at specific time intervals, and the supernatant was separated similarly by centrifugal operation. In the supernatant sample collected at each time, the human insulin concentration was measured by the sandwich ELISA method, and the release amount (%) was calculated in the formula below:

$$\text{Release amount (\%)} = \frac{\text{(human insulin concentration in supernatant (ng/ml)} \times 1.2 \text{ (ml))}}{\text{encapsulated human insulin amount (ng) in 20 mg of particles}} \times 100$$

Figure 2:
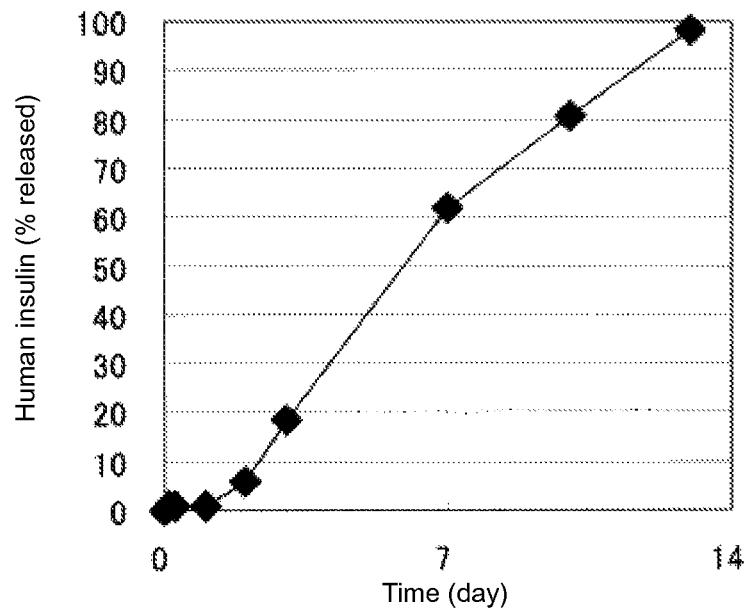
FIG. 2 shows drug release from dextran-PLGA microparticles encapsulating human insulin.

FIG. 2 shows time-course changes of human insulin release. Initial burst was hardly observed, and the drug was released linearly in proportion to the lapse of time, and a favorable profile was observed. The time required for 50% release of the drug was about 6 days.

Example 9

Time-Course Changes of Microparticle Morphology 5 mg of microparticles encapsulating hGH prepared in Example 3 was weighed in an Eppendorf tube, and dispersed in 1 ml of Milli-Q, and was centrifugally separated for 30 minutes at 13,000 rpm, and deprived of the supernatant, and dispersed again in 1 ml of Milli-Q, and centrifugally separated, and the microparticles were cleaned. In the microparticle suspension solution incubated for a specified time, 1 ml of Milli-Q was added, and the solution was centrifugally separated for 30 minutes at 13,000 rpm, deprived of the supernatant, and dispersed again in 1 ml of Milli-Q, and centrifugally separated, and the microparticles were cleaned. The microparticles obtained after cleaning were dispersed in 100 μl of Milli-Q, and 3 μl of the microparticle dispersion liquid was dropped on a silicon substrate, and let stand at room temperature for 10 minutes, and dried for 3 hours in a desiccator. Then, using an ion sputtering device (HITACHI, E-1030), platinum was deposited on the sample surface (deposition time 15 seconds), and the microparticle shape and the surface state were observed by a scanning electron microscope (SEM: HITACHI, S-4800), at an acceleration voltage of 1 kV and a high probe current.

Figure 3:
FIG. 3 shows an SEM image of dextran-PLGA microparticles.
Figure 3:
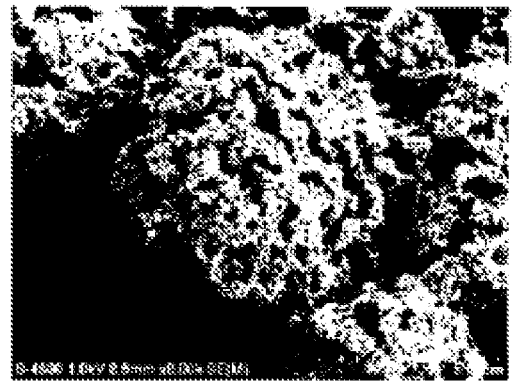

As shown in FIG. 3, right after manufacture, the surface was smooth and spherical, and the particles were obviously deformed after incubation for 13 days at 37° C., many pores were formed, and it was proved that the particles were decomposed gradually along with the progress of release of the drug.

Comparative Example 1

5 mg of polyethylene glycol-poly(epsilon-caprolactone) (average molecular weight of polyethylene glycol is 5,000, average molecular weight of poly(epsilon-caprolactone) is 37,000) was dissolved in 100 μl of dimethyl carbonate to prepare a polymer solution of 50 mg/ml. In this polymer solution, 20 μl of tert-butanol was added, and 20 μl of 2 mg/ml hGH aqueous solution was dropped, and stirred by vortex to prepare a reversed-phase emulsion. This reversed-phase emulsion was frozen preliminarily by liquid nitrogen, and was freeze-dried by using a freeze-drying apparatus (EYELA, FREEZE DRYER FD-1000), at trap cooling temperature of −45° C., and degree of vacuum of 20 Pa, for 24 hours. The obtained solid content was dispersed in 200 μl of dimethyl carbonate to prepare an S/O suspension. This S/O suspension was dropped in 2 ml of aqueous solution containing 10% Pluronic F-68 (a registered trademark of BASF), and was stirred and emulsified in a vortex mixer to prepare an S/O/W type emulsion. From this S/O/W type emulsion, the water-immiscible organic solvent was removed by drying in liquid, and a microparticle dispersion liquid was obtained. The microparticle dispersion liquid was preliminarily frozen by liquid nitrogen, and was freeze-dried by using a freeze-drying apparatus (EYELA, FREEZE DRYER FD-1000), at trap cooling temperature of −45° C., and degree of vacuum of 20 Pa, for 24 hours, and hGH-encapsulating microparticle powder was obtained. The obtained microparticles were observed by a scanning electron microscope (SEM: HITACHI, S-4800), and the average particle diameter was calculated, and the average particle diameter of the microparticles was 8.0 μm.

5 mg of the prepared microparticle powder encapsulating hGH was weighed by using an Eppendorf tube, and was dispersed in 1 ml of Milli-Q, and was centrifuged for 30 minutes at 13,000, deprived of the supernatant, and dispersed again in 1 ml of Milli-Q, and centrifugally separated similarly, and the microparticles were cleaned. The microparticles obtained after cleaning were dispersed in 100 μl of Milli-Q, and 5 μl of the microparticle dispersion liquid was dropped on a silicon substrate, and let stand at room temperature for 10 minutes, and dried for 3 hours in a desiccator. Then, using an ion sputtering device (HITACHI, E-1030), platinum was deposited on the sample surface (deposition time 15 seconds), and the microparticle shape and the surface state were observed by a scanning electron microscope (SEM: HITACHI, S-4800), at an acceleration voltage of 1 kV and a high probe current.

Figure 4:
FIG. 4 shows an SEM image of polyethylene glycol-poly (epsilon-caprolactone) microparticle.
Figure 4:

As shown in FIG. 4, different from the dextran-PLGA microparticle in Example 9, after incubation for 21 days at 37° C., the particles were hardly changed morphologically, and there was a problem in releasing performance of hydrophilic active substance.

Example 10

Hypodermic Administration of Microparticles Encapsulating Human Growth Hormone (hGH) in Mouse 25 mg of dextran-polylactic acid (PLA) (average molecular weight of dextran is 13,000, average molecular weight of PLA is 2,300, number of graft chains of PLA is 10 to 12, compound 3) or dextran-poly(lactic acid-glycolic acid) (PLGA) (average molecular weight of dextran is 13,000, average molecular weight of PLGA 19,000, number of graft chains of PLGA is 7 to 10, compound 7) was dissolved in 500 μl of dimethyl carbonate to prepare a polymer solution of 50 mg/ml. In this polymer solution, 100 μl of tert-butanol was added, and 250 μl of 10 mg/ml hGH aqueous solution was dropped, and stirred by vortex to prepare a reversed-phase emulsion. This reversed-phase emulsion was frozen preliminarily, and was freeze-dried by using a freeze-drying apparatus (EYELA, FREEZE DRYER FD-1000), at trap cooling temperature of −45° C., and degree of vacuum of 20 Pa, for 24 hours. The obtained solid content was dispersed in 1 ml of dimethyl carbonate to prepare an S/O suspension. This S/O suspension was dropped in 10 ml of aqueous solution containing 10% Pluronic F-68 (a registered trademark of BASF), and was stirred and emulsified in a vortex mixer to prepare an S/O/W type emulsion. From this S/O/W type emulsion, the water-immiscible organic solvent was removed by drying in liquid, and a microparticle dispersion liquid was obtained. The microparticle dispersion liquid was preliminarily frozen by liquid nitrogen, and was freeze-dried by using a freeze-drying apparatus (EYELA, FREEZE DRYER FD-1000), at trap cooling temperature of −45° C., and degree of vacuum of 20 Pa, for 24 hours, and hGH-encapsulating microparticle powder was obtained. The obtained microparticles were observed by a scanning electron microscope (SEM: HITACHI, S-4800), and the average particle diameter was calculated, and the average particle diameter was 4.9 μm in the microparticles obtained from compound 3, and 4.2 μm in the microparticles obtained from compound 7.

300 mg of the prepared microparticles was suspended and dispersed in 3 ml of phosphate physiological buffer solution (PBS), and centrifuged for 5 minutes at 80×g to precipitate microparticles, and the supernatant was transferred into other tube. The supernatant was centrifuged again for 5 minutes at 80×g to precipitate the remaining particles, and the supernatant was removed. By re-dispersing in 1 ml of PBS after first time of centrifugal precipitation and second time of centrifugal precipitation, the same centrifugal cleaning operation was repeated three times, and the growth hormone not encapsulated in the microparticles were removed. Finally, the precipitation was dispersed again in 200 μl of PBS, and an administration solution was obtained. The growth hormone amount encapsulated in dextran-PLA microparticle and dextran-PLGA microcapsule was measured by an ELISA kit and the concentration in the cleaning solution was determined, and subtracted from the charged amount, and the amount encapsulated in 300 mg of particles administered per mouse was determined, and the dextran-PLA microparticle was 590 μg, and the dextran-PLGA microparticles was 536 μg.

This solution was injected hypodermically at two positions in the back of 10-week male Balb/C mouse, and the blood was sampled at specific time intervals from the caudal vein. In the sampled blood, heparin of final concentration of 3.31 U/ml was added, and plasma was collected by centrifugal separation for 5 minutes at 5,000 rpm, and the concentration of growth hormone in plasma was measured by using an ELISA kit.

By way of comparison, a non-granulated human growth hormone protein solution (700 μg/0.2 ml) was hypodermically administered in mouse, and the blood was sampled similarly.

To suppress antibody production by administration of human growth hormone, which is a dissimilar protein for mouse, three days before administration of the particle, an immunosuppressant Tacrolimus hydrate (Astellas) was hypodermically administered by 26 μg/mouse, and thereafter 13 μg/mouse was hypodermically administered at the time of the drug administration, and 3 days and 7 days later.

Figure 5:
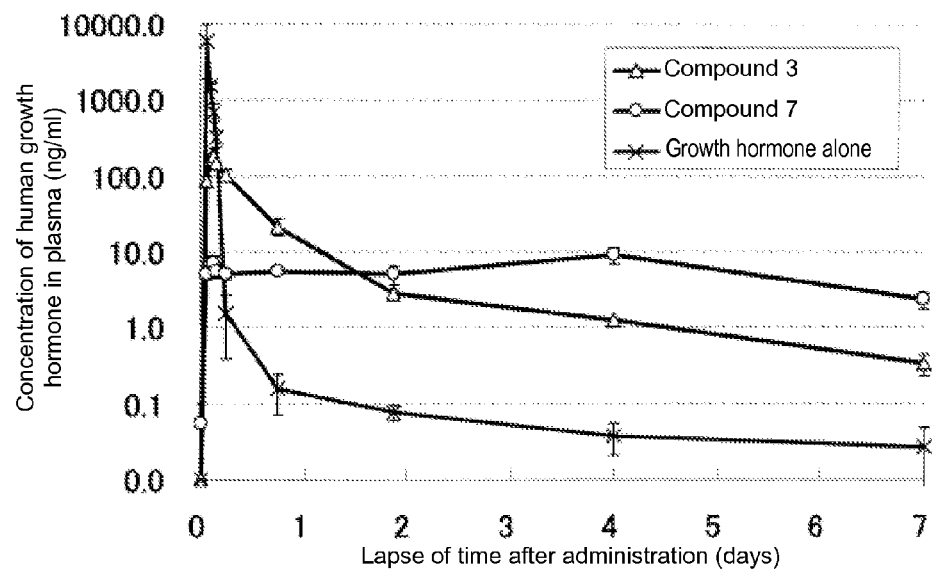
FIG. 5 shows time-course changes of blood drug concentration in mouse administered human growth hormone-encapsulating particles subcutaneously.

FIG. 5 shows time-course changes of concentration of human growth hormone in plasma. In the mouse administered non-granulated drug, the blood level in 1 hour after administration was very high, more than 5,000 ng/ml, and then dropped suddenly, to a level before administration in a day. On the other hand, in the mouse administered the microparticle drug prepared by using dextran-PLA polymer, a transient elevation of blood level right after administration was suppressed to 200 ng/ml or less, and for seven consecutive days, the blood level was sustained at high levels. In dextran-PLA microparticles, transient elevation of concentration after administration was not observed at all, and a nearly specific blood concentration was maintained for seven days, and an excellent sustained-release performance was observed.

Example 11

Hypodermic Administration of Microparticles Encapsulating Human Growth Hormone (hGH) in Mouse (Pharmacological Activity Evaluation)

2 mg of dextran-poly(lactic acid-glycolic acid) (PLGA) (average molecular weight of dextran is 13,000, average molecular weight of PLGA is 1,900, number of graft chains of PLGA is 7 to 10, compound 7) was dissolved in 500 µl of dimethyl carbonate to prepare a polymer solution of 50 mg/ml. In this polymer solution, 100 µl of tert-butanol was added, and 250 µl of 10 mg/ml hGH aqueous solution was dropped, and stirred by vortex to prepare a reversed-phase emulsion. This reversed-phase emulsion was frozen preliminarily by liquid nitrogen, and was freeze-dried by using a freeze-drying apparatus (EYELA, FREEZE DRYER FD-1000), at trap cooling temperature of −45° C., and degree of vacuum of 20 Pa, for 24 hours. The obtained solid content was dispersed in 1 ml of dimethyl carbonate to prepare an S/O suspension. This S/O suspension was dropped in 10 ml of aqueous solution containing 10% Pluronic F-68 (a registered trademark of BASF), and was stirred and emulsified in a vortex mixer to prepare an S/O/W type emulsion. From this S/O/W type emulsion, the water-immiscible organic solvent was removed by drying in liquid, and a microparticle dispersion liquid was obtained. The microparticle dispersion liquid was preliminarily frozen by liquid nitrogen, and was freeze-dried by using a freeze-drying apparatus (EYELA, FREEZE DRYER FD-1000), at trap cooling temperature of −45° C., and degree of vacuum of 20 Pa, for 24 hours, and hGH-encapsulating microparticle powder was obtained. The obtained microparticles were observed by a scanning electron microscope (SEM: HITACHI, S-4800), and the average particle diameter was calculated, and the average particle diameter of the obtained microparticles was 4.1 µm.

300 mg of the prepared microparticles was suspended and dispersed in 3 ml of phosphate physiological buffer solution (PBS), and particles were precipitated by centrifugal separation for 5 minutes at 80×g, and a supernatant was transferred in other tube. The supernatant was centrifugally separated again for 5 minutes at 80×g, and the remaining particles were precipitated, and the supernatant was removed. The first centrifugal precipitation and the second centrifugal precipitation were combined, and dispersed again in 1 ml of PBS, and similarly a third centrifugal operation was conducted, and the growth hormone not encapsulated in the particles was removed. Finally, the precipitation was dispersed again in 200 µl of PBS to prepare an administration solution.

This solution was hypodermically injected in the back of 8-week-old pituitary gland extracted mouse (from Japan SLC), and the blood was sampled at specific intervals from the caudal vein. In the sampled blood, heparin of final concentration of 3.3 IU/ml was added, and centrifuged for 5 minutes at 5,000 rpm, and the plasma was collected, and the growth hormone concentration in plasma and the mouse IGF-1 concentration were measured by ELISA method.

By way of comparison, a non-granulated human growth hormone protein solution (700 µg/0.2 ml) was hypodermically administered in mouse, and the blood was sampled similarly.

To suppress antibody production by administration of human growth hormone, which is a foreign protein for mouse, three days before administration of the particle, an immunosuppressant Tacrolimus hydrate (Astellas) was hypodermically administered by 26 µg/mouse, and thereafter 13 µg/mouse was hypodermically administered at the time of the drug administration, and 3 days and 7 days later.

Figure 6:
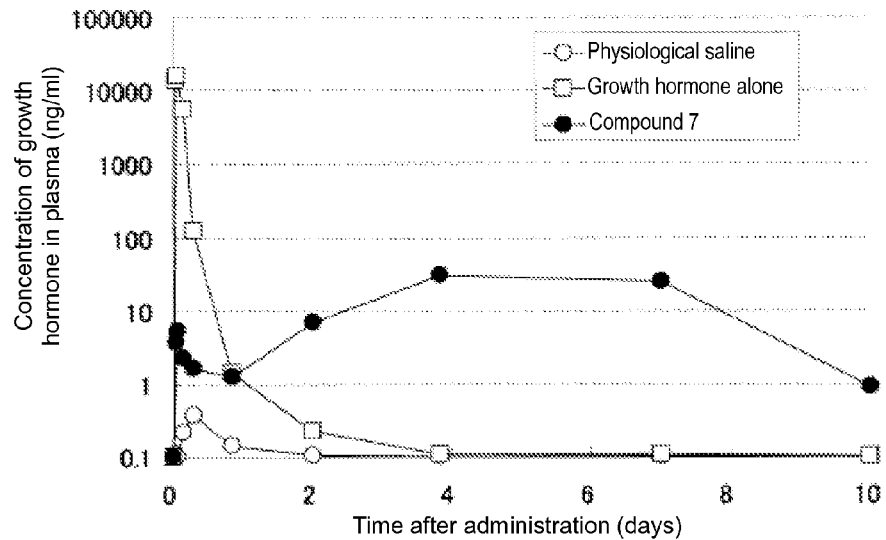
FIG. 6 shows time-course changes of blood drug concentration in mouse administered human growth hormone-encapsulating microparticles subcutaneously.
Figure 7:
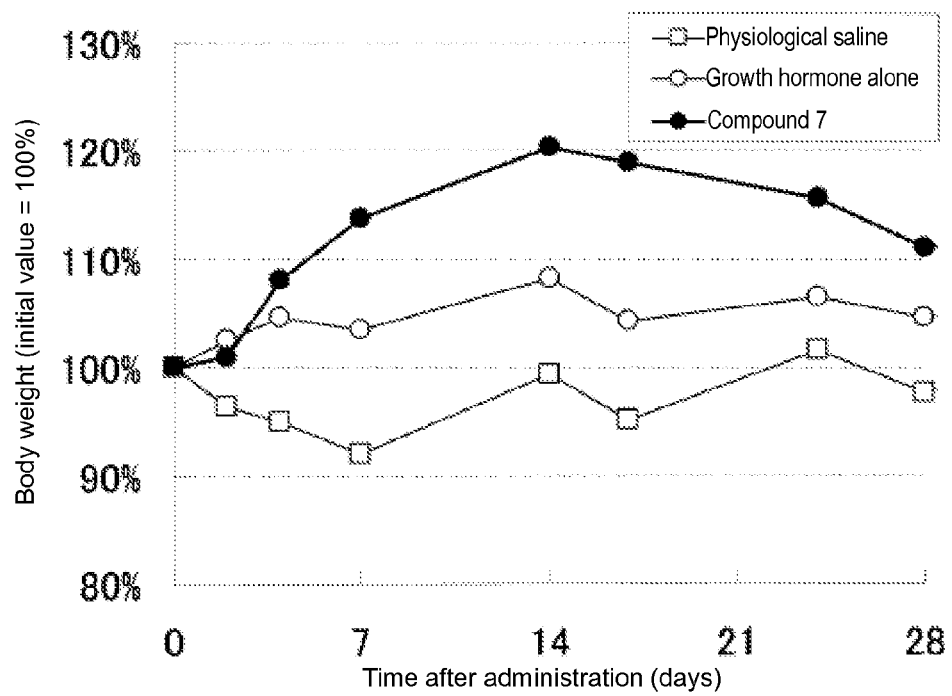
FIG. 7 shows changes of body weight in mouse administered human growth hormone-encapsulating microparticles subcutaneously.

FIG. 6 shows time-course changes of concentration of human growth hormone in plasma. In the mouse administered non-granulated drug, the blood level in 1 hour after administration was very high, and then dropped suddenly, to a level before administration in two days. On the other hand, in the dextran-PLGA microparticle, a transient concentration elevation right after administration was suppressed low, and for ten consecutive days after administration, the concentration in plasma was sustained at high levels. At this time, the body weight changes of mouse are shown in FIG. 7. In the mouse administered the growth hormone alone, the body weight increased was suppressed at about 5%, but in the mouse administered the dextran-PLGA microparticles, the body weight increased about 20%.

Figure 8:
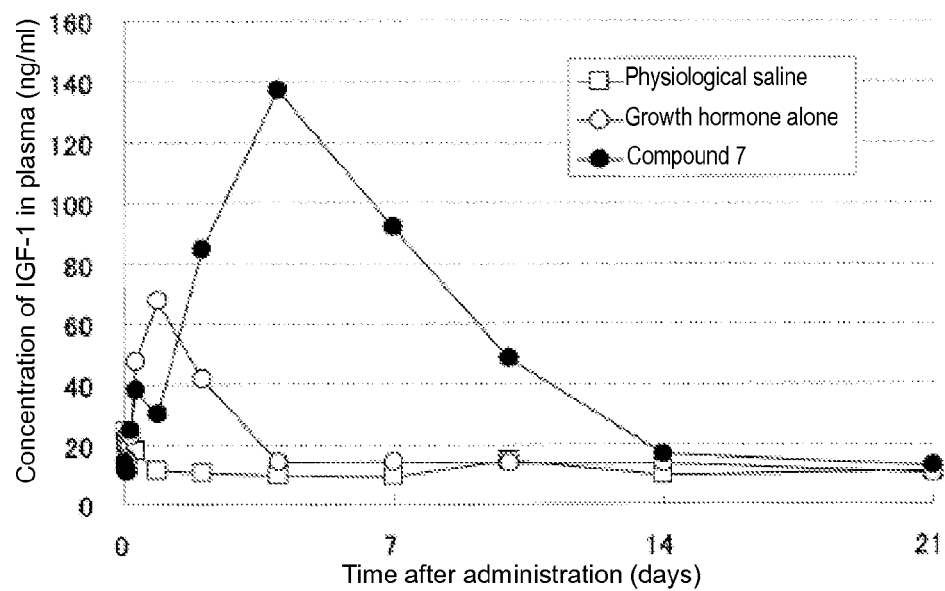
FIG. 8 shows time-course changes of blood IGF-1 concentration in mouse administered human growth hormone-encapsulating microparticles subcutaneously.

FIG. 8 shows the IGF-1 concentration in plasma. The IGF-1 concentration in plasma is correlated with the human growth hormone concentration in blood, and in the mouse administered the dextran-PLGA microparticles, high levels were maintained for ten days after administration.

Example 12

Analysis of Drug Release Speed in Buffer Solution from Microparticles Encapsulating Exendin-4 (GLP-1 Receptor Agonist)

25 mg of dextran-poly(lactic acid-glycolic acid) (PLGA) (average molecular weight of dextran is 13,000, average molecular weight of PLGA is 3,250 (compound 8) or 6,442 (compound 9), number of graft chains of PLGA is 21 (compound 8) or 15 (compound 9) was dissolved in 500 µl of dimethyl carbonate to prepare a polymer solution of 50 mg/ml. In this polymer solution, 100 µl of tert-butanol was added, and 250 µl of 10 mg/ml Exendin-4 (synthesized by commission with Sigma Genosys) was dropped, and stirred by vortex to prepare a reversed-phase emulsion. This reversed-phase emulsion was frozen preliminarily by liquid nitrogen, and was freeze-dried by using a freeze-drying apparatus (EYELA, FREEZE DRYER FD-1000), at trap cooling temperature of −45° C., and degree of vacuum of 20 Pa, for 24 hours. The obtained solid content was dispersed in 1 ml of dimethyl carbonate to prepare an S/O suspension. This S/O suspension was dropped in 10 ml of aqueous solution containing 10% Pluronic F-68 (a registered trademark of BASF), and was stirred and emulsified in a vortex mixer to prepare an S/O/W type emulsion. From this S/O/W type emulsion, the water-immiscible organic solvent was removed by drying in liquid, and a microparticle dispersion liquid was obtained. The microparticle dispersion liquid was preliminarily frozen by liquid nitrogen, and was freeze-dried by using a freeze-drying apparatus (EYELA, FREEZE DRYER FD-1000), at trap cooling temperature of −45° C., and degree of vacuum of 20 Pa, for 24 hours, and Exendin-4-encapsulating microparticle powder was obtained. The obtained microparticles were observed by a scanning electron microscope (SEM: HITACHI, S-4800), and the average particle diameter was calculated, and the average particle diameter was 4.3 µm in compound 8, and 4.5 µm in compound 9.

These microparticles were cleaned three times according to the method in Example 4, and were suspended and dispersed in 1.2 ml of buffer solution A. From this solution, a part (40 µl) was transferred into other tube, and was centrifuged for 10 minutes at 18,000×g to precipitate the particles, and 30 µl of supernatant was collected in a different tube (0-hour sample). The remaining particle suspension was put in a 1.5 ml Eppendorf tube, and was rolled and mixed slowly in an incubator at 37° C., by using a rotator at a speed of 6 rpm. From this solution, a small portion (40 µl) was dispensed at specific time intervals, and the supernatant was separated similarly by centrifugal operation. In the supernatant sample collected at each time, the Exendin-4 concentration was measured by the ELISA method, and the release amount (%) was calculated in the formula below:

$$\text{Release amount (\%)} = \frac{(\text{Exendin-4 concentration in supernatant (ng/ml)} \times 1.2 \text{ (ml)})}{\text{encapsulated Exendin-4 amount (ng) in 20 mg of particles}} \times 100$$

Figure 9:
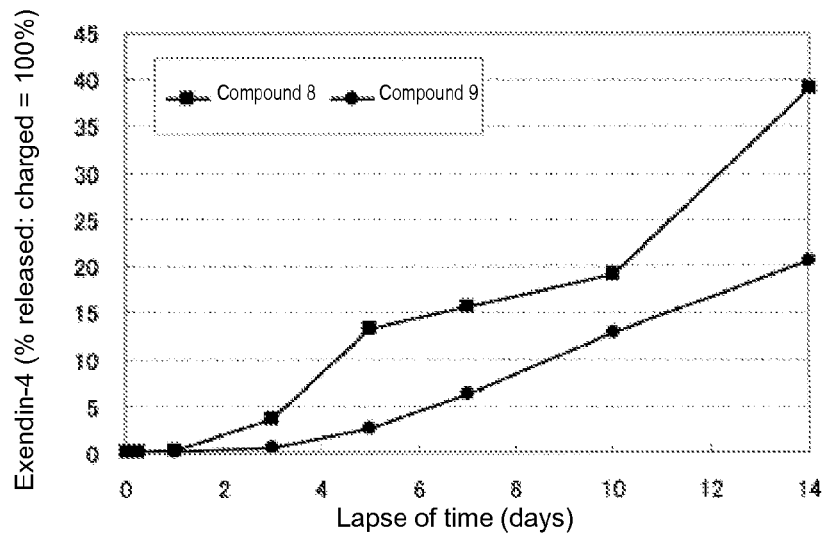
FIG. 9 shows drug release in a buffer solution of Exendin-4-encapsulating microparticles.

FIG. 9 shows time-course changes of drug release from microparticles manufactured by using each dextran-PLGA polymer. In both microparticles, initial burst was hardly observed, and the drug was released linearly in proportion to the lapse of time, and a favorable profile was observed.

Example 13

Hypodermic Administration of Microparticles Encapsulating Exendin-4 (GLP-1 Receptor Agonist) in Mouse 300 mg of microparticles in Example 12 was suspended and dispersed in 3 ml of phosphate physiological buffer solution (PBS), and the microparticles were precipitated by centrifugal operation for 5 minutes at 80×g, and a supernatant was transferred in other tube. The supernatant was centrifugally separated again for 5 minutes at 80×g, and the remaining particles were precipitated, and the supernatant was removed. The first centrifugal precipitation and the second centrifugal precipitation were combined, and dispersed again in 1 ml of PBS, and similarly a third centrifugal operation was conducted, and the Exendin-4 not encapsulated in the particles was removed. Finally, the precipitation was dispersed again in 200 µl of PBS to prepare an administration solution.

This solution was hypodermically injected in the back of 8-week-old SCID mouse (CB17/lcr-Prkdcscid/CrlCrlk) (from Crea Japan Inc.), and the blood was sampled at specific intervals from the caudal vein. In the sampled blood, heparin of final concentration of 3.3 IU/ml was added, and centrifuged for 5 minutes at 5,000 rpm, and the plasma was collected, and the Exendin-4 concentration in plasma was measured by ELISA method. By way of comparison, a non-granulated Exendin-4 solution (700 µg/0.2 ml) was hypodermically administered in mouse, and the blood was sampled similarly.

Figure 10:
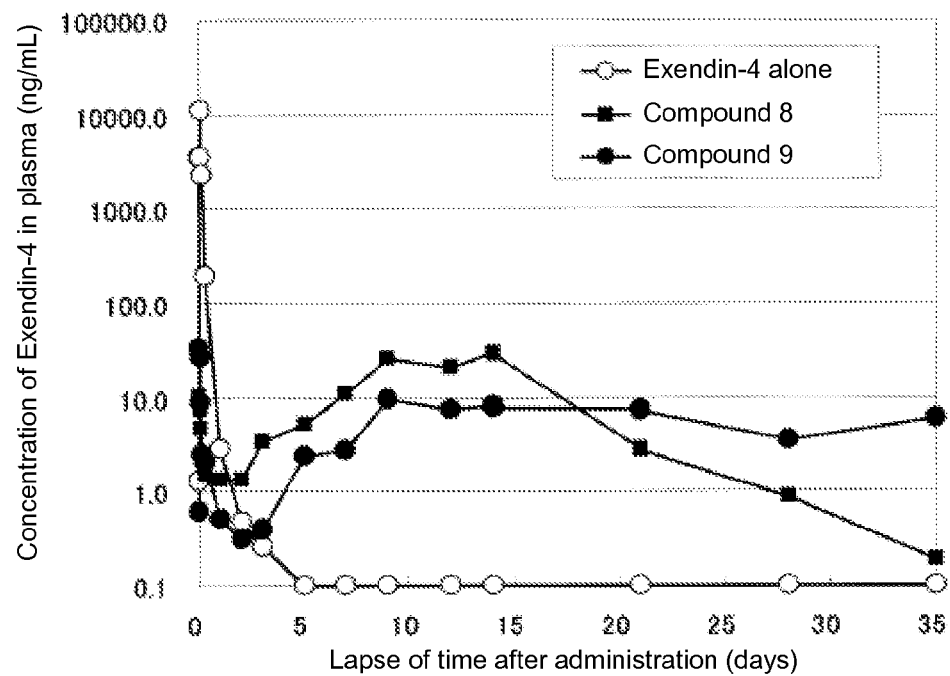
FIG. 10 shows time-course changes of blood drug concentration in mouse administered Exendin-4-encapsulating microparticles subcutaneously.

FIG. 10 shows time-course changes of concentration of Exendin-4 in plasma. In the mouse administered non-granulated drug, the blood level in 1 hour after administration was very high, and then dropped suddenly, to a level before administration. On the other hand, in the dextran-PLGA microparticle, a transient concentration elevation after administration was suppressed low, and for five consecutive weeks after administration, the concentration in plasma was sustained at high levels.

Example 14

Synthesis of dextran-poly(lactic acid-glycolic acid) (PLGA)

14.1 Synthesis of TMS-dextran-PLGA (compound 10, compound 11, compound 12, compound 13)

Compound 1 (0.5 g) and tert-butoxy potassium (35 mg) were dried for 1 hour at reduced pressure, and tetrahydrofurane (10 ml) was added, and the mixture was stirred for 1 hour at room temperature. In this solution, tetrahydrofurane (15 ml) solution of (DL)-lactide (0.558 g) and glycolide (0.45 g) was dropped, and the mixture was stirred for 5 minutes. After completion of reaction, the solvent was concentrated at reduced pressure, and purified by reprecipitation by a chloroform-methanol system, and TMS-dextran-PLGA (1.96 g) was obtained as white solid content (compound 10).

In a similar method, by the charging amount of (DL)-lactide (0.67 g) and glycolide (0.54 g), compound 11 was synthesized.

In a similar method, by the charging amount of (DL)-lactide (0.781 g) and glycolide (0.629 g), compound 12 was synthesized.

In a similar method, by the charging amount of (DL)-lactide (1.123 g) and glycolide (0.9 g), compound 13 was synthesized.

14.2 Synthesis of dextran-PLGA (compound 14, compound 15, compound 16, compound 17)

In chloroform solution (10 mL) of compound 10, trifluoroacetic acid (1 mL) was added, and stirred for 30 minutes at room temperature. The solvent was distilled away at reduced pressure, and the residue was dissolved in chloroform (10 ml), and dropped into diethyl ether cooled to 0° C., and the product was deposited. The deposition matter was filtered away, and concentrated at reduced pressure, and dextran-PLGA (0.44 g) was obtained (compound 14).

From compounds 11, 12, and 13, dextran-PLGA products were obtained by a similar method (compound 5, compound 16, compound 17). The weight-average molecular weight and the number-average molecular weight of the polymer of compounds 14 to 17 were determined by GPC measurement (column Toso TSK-gel α-5000×2, DMF system solvent, detector RI, standard product, pullulan). The average molecular weight of the graft chain and the number of graft chains were determined by $^1$H-NMR measurement.

As for compound 14, the weight-average molecular weight was 99,462, the number-average molecular weight was 85,101, the graft chain number-average molecular weight was 2,167, and the number of graft chains was 33.

As for compound 15, the weight-average molecular weight was 107,779, the number-average molecular weight was 92,134, the graft chain number-average molecular weight was 3,127, and the number of graft chains was 25.

As for compound 16, the weight-average molecular weight was 121,281, the number-average molecular weight was 101,873, the graft chain number-average molecular weight was 3,000, and the number of graft chains was 30.

As for compound 17, the weight-average molecular weight was 144,838, the number-average molecular weight was 122,151, the graft chain number-average molecular weight was 4,864, and the number of graft chains was 22.

Example 15

Preparation Method of Microparticles Encapsulating Human Growth Hormone (hGH)

5 mg of each dextran-poly(lactic acid-glycolic acid) (dextran-PLGA polymer, compounds 14 to 17) of Example 14 was dissolved in 100 μl of dimethyl carbonate to prepare a polymer solution of 50 mg/ml. In this polymer solution, 20 μl of tert-butanol was added, and 50 μl of 1 mg/ml hGH aqueous solution was dropped, and stirred by vortex to prepare a reversed-phase emulsion. This reversed-phase emulsion was frozen preliminarily by liquid nitrogen, and was freeze-dried by using a freeze-drying apparatus (EYELA, FREEZE DRYER FD-1000), at trap cooling temperature of −45° C., and degree of vacuum of 20 Pa, for 24 hours. The obtained solid content was dispersed in 200 μl of dimethyl carbonate to prepare an S/O suspension. This S/O suspension was dropped in 2 ml of aqueous solution containing 10% Pluronic F-68 (a registered trademark of BASF), and was stirred and emulsified in a vortex mixer to prepare an S/O/W type emulsion. From this S/O/W type emulsion, the water-immiscible organic solvent was removed by drying in liquid, and a microparticle dispersion liquid was obtained. The microparticle dispersion liquid was preliminarily frozen by liquid nitrogen, and was freeze-dried by using a freeze-drying apparatus (EYELA, FREEZE DRYER FD-1000), at trap cooling temperature of −45° C., and degree of vacuum of 20 Pa, for 24 hours, and hGH-encapsulating microparticle powder was obtained. The obtained microparticles were observed by a scanning electron microscope (SEM: HITACHI, S-4800), and the average particle diameter was calculated, and the average particle diameter of the microparticles was within a range of 1.0 to 10 μm.

Example 16

Measurement of Drug Encapsulation Efficiency of Microparticles Encapsulating Human Growth Hormone (hGH)

20 mg of microparticles encapsulating human growth hormone prepared in the method of Example 15 by using each dextran-PLGA polymer (compounds 14 to 17) was weighed by using a 1.5 ml Eppendorf tube, and was dissolved in 1 ml of buffer solution A (PBS containing 0.1% bovine serum albumin, 0.1% Pluronic F-68 (a registered trademark of BASF), and 0.02% sodium azide), and was centrifuged for 10 minutes at 18,000×g, and was separated into particles (precipitation) and a supernatant. The supernatant was collected in other tube, and the particles were suspended again in 1 ml of buffer solution, and the centrifugal operation and the separation into particles and a supernatant were conducted again in the same conditions. This cleaning operation was repeated once more (total three times of centrifugal operation), and the human growth hormone concentration of each supernatant collected by the centrifugal operations was measured by using an ELISA kit (manufactured by R&D Systems). From the charged amount of hGH at the time of preparation of particles (particle weight 20 mg), the hGH total amount of three supernatants by centrifugal operations was subtracted, and the encapsulation efficiency was calculated according to the formula below:

$$\text{Encapsulation efficiency (\%)} = \frac{(\text{charged } hGH \text{ amount (ng)} - hGH \text{ amount total in supernatants (ng)})}{\text{charged } hGH \text{ amount (ng)}} \times 100.$$

In dextran-PLGA microparticles, the encapsulation efficiency of hGH was 87.5% in microparticles of compound 14, 94.2% in microparticles of compound 15, 95.7% in microparticles of compound 16, and 97.5% in microparticles of compound 17, and it was proved that the protein drug can be encapsulated at a high efficiency in all microparticles.

Comparative Example 2

Manufacture of Particles Encapsulating Growth Hormone and Measurement of Drug Encapsulation Efficiency 10 mg dextran-poly(lactic acid-glycolic acid)(PLGA) (compound 14 or compound 17) was dissolved in 2 mL of ethyl acetate to prepare a polymer solution. In this polymer solution, 100 μL of 0.5 mg/mL hGH aqueous solution was dropped, and stirred. After stirring operation, the solution was added to 20 mL of dioxane. The solvent was evaporated, and the solution was concentrated to about 2 mL, and the particle dispersion liquid was added to water containing 500 mg Pluronic F-68 (a registered trademark of BASF). The sample was freeze-dried, and 1 mL of water is added to 50 mg of the sample, and the particles were dispersed again, and non-associated hydrophilic active substance containing particles were obtained. The average particle diameter of the particles was measured by a dynamic light scatter method by using an apparatus ELS-Z (manufactured by Otsuka Denshi), and the drug encapsulation efficiency was determined same as in Example 16.

As a result, in the particles of compound 14, the average particle diameter was 190.5 nm, and the encapsulation efficiency was 73%, and in the particles of compound 17, the average particle diameter was 197.5 nm, and the encapsulation efficiency was 70%, and the encapsulation efficiency was lower than in the microparticles of Example 16.

Example 17

Analysis of In-Vitro Drug Release Speed from Microparticles Encapsulating Human Growth Hormone (hGH)

Particles cleaned three times in Example 16 were suspended and dispersed in 1.2 ml of buffer solution A. From this solution, a part (40 μl) was transferred into other tube, and was centrifuged for 10 minutes at 18,000×g to precipitate the particles, and 30 μl of supernatant was collected in a different tube (0-hour sample). The remaining particle suspension was put in a 1.5 ml Eppendorf tube, and was rolled and mixed slowly in an incubator at 37° C., by using a rotator at a speed of 6 rpm. From this solution, a small portion (40 μl) was dispensed at specific time intervals, and the supernatant was separated similarly by centrifugal operation. In the supernatant sample collected at each time, the hGH concentration was measured by the ELISA kit, and the release amount (%) was calculated in the formula below:

Release amount (%) =

$$\frac{(hGH \text{ concentration in supernatant (ng/ml)} \times 1.2 \text{ (ml)})}{\text{encapsulated } hGH \text{ amount (ng) in 20 mg of particles}} \times 100$$

Figure 11:
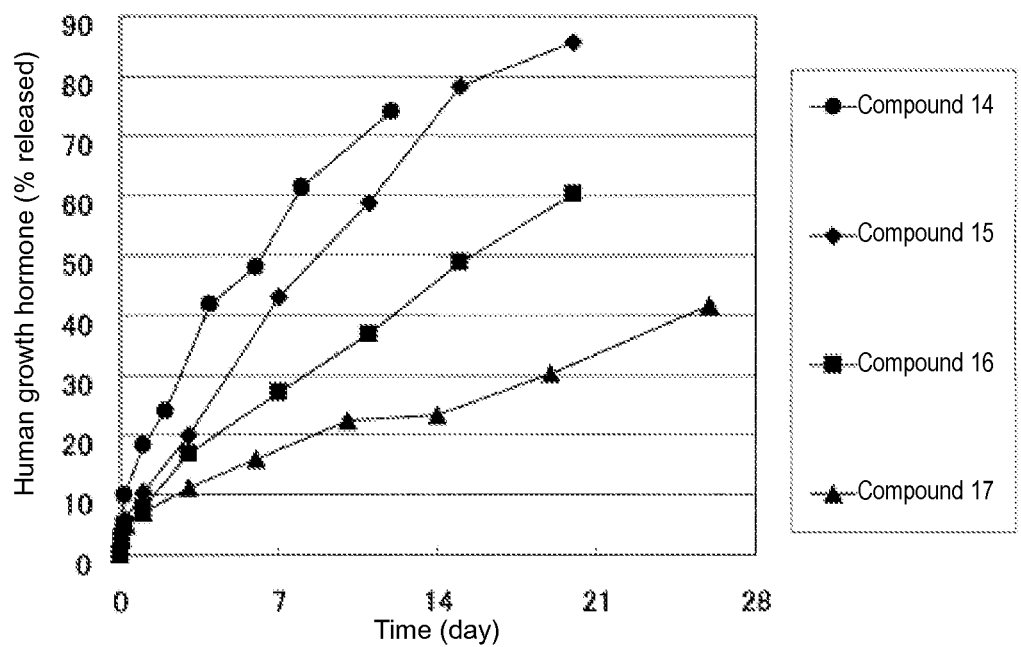
FIG. 11 shows drug release from human growth hormone-encapsulating associated particles microparticles.

FIG. 11 shows time-course changes of drug release from microparticles manufactured in Example 15. In these microparticles, initial burst was hardly observed, and the drug was released linearly in proportion to the lapse of time, and a favorable profile was observed. The time required for 50% release of the drug was about 6 days in microparticles of compound 14, about 9 days in microparticles of compound 15, about 16 days in microparticles of compound 16, and about 1 month in microparticles of compound 17, and it was suggested that the release speed could be controlled by changing the charged amount of lactide and glycolide at the time of synthesis of TMS-dextran-PLGA.

Example 18

Preparation Method of Microparticles Encapsulating Fluoresceine Labeled Dextran (FD40) Different in Particle Diameter 5 mg of dextran-poly(lactic acid-glycolic acid) (PLGA) (compound 7) of Example 2 was dissolved in 100 µl of dimethyl carbonate to prepare a polymer solution of 50 mg/ml. In this polymer solution, 20 µl of tert-butanol was added, and 20 µl of 1 mg/ml FD40 aqueous solution was dropped, and stirred by vortex to prepare a reversed-phase emulsion. This reversed-phase emulsion was frozen preliminarily by liquid nitrogen, and was freeze-dried by using a freeze-drying apparatus (EYELA, FREEZE DRYER FD-1000), at trap cooling temperature of −45° C., and degree of vacuum of 20 Pa, for 24 hours. The obtained solid content was dispersed in 50 µl, 100 µl, 200 µl, 350 µl, 500 µl, 1 ml, 2 ml, and 6 ml of dimethyl carbonate to prepare an S/O suspension. This S/O suspension was dropped in 2 ml of aqueous solution containing 10% Pluronic F-68 (a registered trademark of BASF), and was stirred and emulsified in a vortex mixer to prepare an S/O/W type emulsion. From this S/O/W type emulsion, the water immiscible organic solvent was removed by drying in liquid, and a microparticle dispersion liquid was obtained. The microparticle dispersion liquid was preliminarily frozen by liquid nitrogen, and was freeze-dried by using a freeze-drying apparatus (EYELA, FREEZE DRYER FD-1000), at trap cooling temperature of −45° C., and degree of vacuum of 20 Pa, for 24 hours, and FD40-encapsulating microparticle powder was obtained. The obtained microparticles were observed by a scanning electron microscope (SEM: HITACHI, S-4800), and the average particle diameter was calculated.

Figure 12:
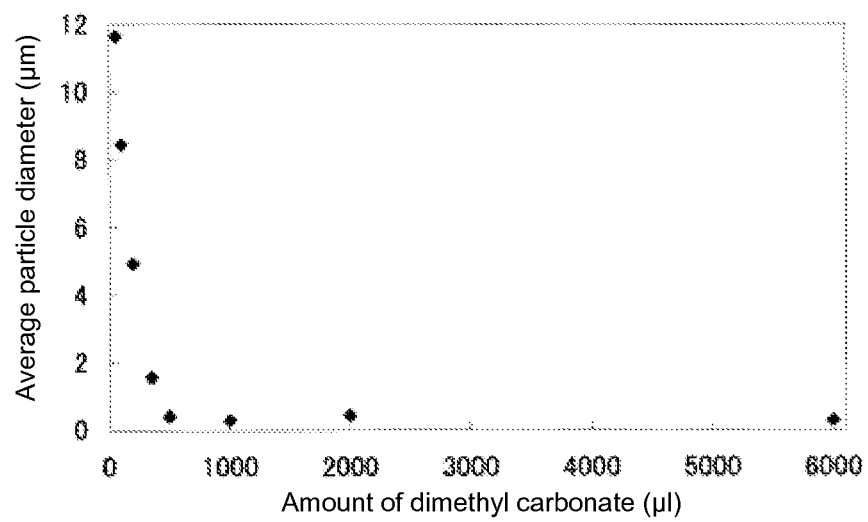
FIG. 12 shows the relation between particle diameter and amount of dimethyl carbonate added at the time of preparation of S/O/W type emulsion.

FIG. 12 shows the correlation between the average particle diameter and the amount of dimethyl carbonate added at the time of preparation of S/O/W type emulsion. In a range from 50 µl to 500 µl, along with increase of dimethyl carbonate amount, decline of the average particle diameter was observed. From 500 µl to 6 ml, almost no difference was observed in the average particle diameter.

Example 19

Synthesis of PEG-PLGA Polymer (PEG2k Series)

Polyethylene glycol monomethyl ether (manufactured by NOF Corp., SUNBRIGHT MEH-20H, number-average molecular weight: 1,862, Mw/Mn=1.03), (DL)-lactide, and glycolide were mixed in the specified composition shown in Table 1, and heated at 140° C. After stirring for 20 minutes, tin octylate(II) was added (by 0.05 wt. % to polyethylene glycol monomethyl ether), and stirred for 3 hours at 180° C. The reaction solution was returned to room temperature, and was dissolved in chloroform (to a concentration of about 100 mg/ml), and precipitated again and refined in diethyl ether cooled at 0° C., and the obtained solid content was filtered, decompressed, and dried, and PEG-PLGA polymer was obtained as white or pale brown solid content. The number-average molecular weight of this polymer was determined by $^1$H-NMR (Table 1).

TABLE 1

Raw material charged amount and reaction results of synthesis of PEG-PLGA polymer (PEG2k series)

| Charged amount (g) | | | | Molecular | Polymer composition (molecular weight of PEG)-(molecular |
|---|---|---|---|---|---|
| PEG | (DL)-lactide | Glycolide | Yield (g) | weight ($^1$H-NMR) | weight of PLGA) |
| 0.8 | 1.44 | 1.16 | 4.74 | 13500 | 2k-11.5k |
| 0.4 | 1.44 | 1.16 | 2.65 | 23560 | 2k-21.5k |
| 0.2 | 1.44 | 1.16 | 2.52 | 52700 | 2k-50.7k |

Example 20

Synthesis of PEG-PLGA Polymer (PEG5k Series)

Polyethylene glycol monomethyl ether (manufactured by NOF Corp., SUNBRIGHT MEH-20H, number-average molecular weight: 5,128, Mw/Mn=1.02), (DL)-lactide, and glycolide were mixed in the specified composition shown in Table 2, and heated at 140° C. After stirring for 20 minutes, tin octylate(II) was added (by 0.05 wt. % to polyethylene glycol mono-methyl ether), and stirred for 3 hours at 180° C. The reaction solution was returned to room temperature, and was dissolved in chloroform (to a concentration of about 100 mg/ml), and precipitated again and refined in diethyl ether cooled at 0° C., and the obtained solid content was filtered, decompressed, and dried, and PEG-PLGA polymer was obtained as white or pale brown solid content. The number-average molecular weight of this polymer was determined by $^1$H-NMR (Table 2).

TABLE 2

Raw material charged amount and reaction results of synthesis of PEG-PLGA polymer (PEG5k series)

| Charged amount (g) | | | Yield (g) | Molecular weight ($^1$H-NMR) | Polymer composition (molecular weight of PEG)-(molecular weight of PLGA) |
|---|---|---|---|---|---|
| PEG | (DL)-lactide | Glycolide | | | |
| 0.5 | 0.72 | 0.58 | 1.31 | 15600 | 5k-10k |
| 0.5 | 1.44 | 1.16 | 2.51 | 28400 | 5k-23k |
| 0.33 | 1.44 | 1.16 | 2.1 | 37500 | 5k-32.5k |
| 0.6 | 2.88 | 2.32 | 5.5 | 44400 | 5k-39.4k |
| 0.27 | 1.44 | 1.16 | 2.62 | 52000 | 5k-47k |
| 0.2 | 1.44 | 1.16 | 2.52 | 66000 | 5k-61k |
| 0.3 | 2.16 | 1.74 | 4.07 | 69935 | 5k-65k |
| 0.8 | 2.16 | 1.74 | 3.79 | 59555 | 5k-55k |
| 0.1 | 1.15 | 0.93 | — | 109381 | 5k-105k |

Example 21

Synthesis of PEG-PLGA Polymer (PEG10k Series)

Polyethylene glycol monomethyl ether (manufactured by NOF Corp., SUNBRIGHT MEH-10H, number-average molecular weight: 9,975, Mw/Mn=1.02), (DL)-lactide, and glycolide were mixed in the specified composition shown in Table 3, and heated at 140° C. After stirring for 20 minutes, tin octylate(II) was added (by 0.05 wt. % to polyethylene glycol monomethyl ether), and stirred for 3 hours at 180° C. The reaction solution was returned to room temperature, and was dissolved in chloroform (to a concentration of about 100 mg/ml), and precipitated again and refined in diethyl ether cooled at 0° C., and the obtained solid content was filtered, decompressed, and dried, and PEG-PLGA polymer was obtained as white or pale brown solid content. The number-average molecular weight of this polymer was determined by $^1$H-NMR (Table 3).

TABLE 3

Raw material charged amount and reaction results of synthesis of PEG-PLGA polymer (PEG10k series)

| Charged amount (g) | | | Yield (g) | Molecular weight ($^1$H-NMR) | Polymer composition (molecular weight of PEG)-(molecular weight of PLGA) |
|---|---|---|---|---|---|
| PEG | (DL)-lactide | Glycolide | | | |
| 0.5 | 1.44 | 1.16 | 2.3 | 49000 | 10k-39k |
| 0.25 | 1.44 | 1.16 | 2.48 | 105000 | 10k-95k |

Example 22

Figure 14:
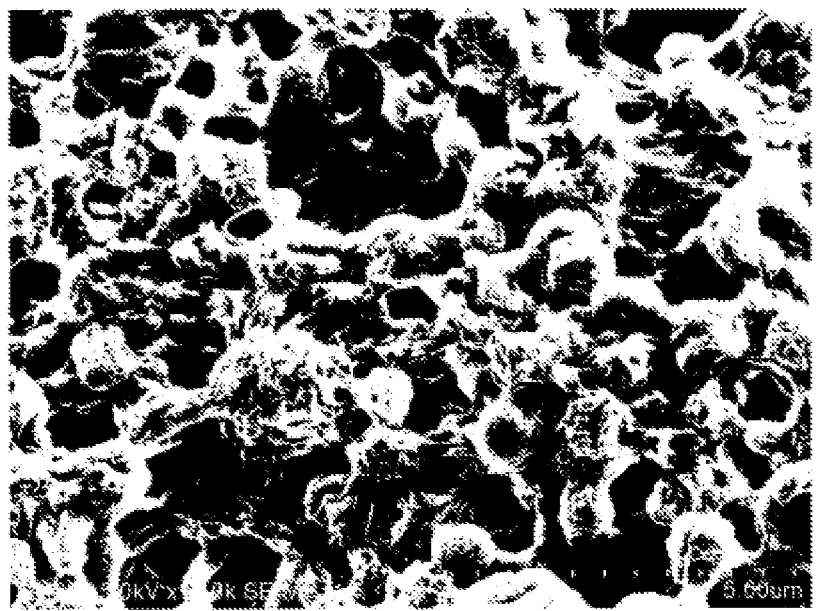
FIG. 14 shows an SEM image of microparticle powder prepared from PEG-PLGA polymer (5k-10k).
Figure 15:
FIG. 15 shows an SEM image of microparticle powder prepared from PEG-PLGA polymer (5k-61k).

Preparation Method of FD40-Encapsulating Microparticles 5 mg of PEG-PLGA polymer prepared in Examples 19 to 21 was dissolved in 100 μl of dimethyl carbonate to prepare a polymer solution of 50 mg/ml. In this polymer solution, 20 μl of tert-butanol was added, a specified amount of 10 mg/ml FD40 aqueous solution as shown in Table 4 was added, and stirred to prepare a reversed-phase emulsion. This reversed-phase emulsion was frozen preliminarily by liquid nitrogen, and was freeze-dried by using a freeze-drying apparatus (EYELA, FREEZE DRYER FD-1000), at trap cooling temperature of −45° C., and degree of vacuum of 20 Pa, for 24 hours. The obtained solid content was dispersed in 200 μl of dimethyl carbonate to prepare an S/O suspension. This S/O suspension was dropped in 2 ml of aqueous solution containing 10% Pluronic F-68 (a registered trademark of BASF), and was stirred and emulsified in a vortex mixer to prepare an S/O/W type emulsion. From this S/O/W type emulsion, the water-immiscible organic solvent was removed by drying in liquid, and a microparticle dispersion liquid was obtained. The microparticle dispersion liquid was preliminarily frozen by liquid nitrogen, and was freeze-dried by using a freeze-drying apparatus (EYELA, FREEZE DRYER FD-1000), at trap cooling temperature of −45° C., and degree of vacuum of 20 Pa, for 24 hours, and FD40-encapsulating microparticle powder was obtained, and a part thereof was observed by a scanning electron microscope (SEM: HITACHI, S-4800), and the average particle diameter was calculated (Table 4). SEM images of the powder prepared from the PEG-PLGA polymer of 5k to 10k are shown in FIG. 14, and SEM images of the powder prepared from the PEG-PLGA polymer of 5k to 61k are shown in FIG. 15.

TABLE 4

FD40 aqueous solution amount to be added to each polymer, and average particle diameter of obtained microparticles.

| PEG-PLGA composition | FD40 aqueous solution amount (μL) | Average particle diameter (μm) |
|---|---|---|
| 2k-11.5k | 13 | — |
| 2k-21.5k | 12 | — |
| 2k-50.7k | 12 | — |
| 5k-10k | 20 | — |
| 5k-23k | 20 | 4.6 |
| 5k-32.5k | 20 | 4.3 |
| 5k-39.4k | 20 | — |
| 5k-47k | 20 | 4.2 |
| 5k-61k | 20 | 3.9 |
| 5k-65k | 20 | 3.2 |

TABLE 4-continued

FD40 aqueous solution amount to be added to each polymer,
and average particle diameter of obtained microparticles.

| PEG-PLGA composition | FD40 aqueous solution amount (μL) | Average particle diameter (μm) |
|---|---|---|
| 10k-39k | 18 | 4.8 |
| 10k-95k | 15 | 4.5 |

Example 23

Measurement of Encapsulation Efficiency of FD40-Encapsulating Microparticles

Microparticle (5 mg) encapsulating FD40 prepared in the method of Example 22 by using the PEG-PLGA polymer was weighed by using a 1.5 ml Eppendorf tube, and was dispersed in Milli-Q (1 ml), and centrifuged for 30 minutes, and separated into a supernatant containing non-encapsulated FD40 and FD40-encapsulating particles, and collected. The collected FD40-encapsulating particles were dissolved in N,N-dimethyl formamide (250 μl), and the particles were disintegrated. The supernatant containing non-encapsulated FD40 and N,N-dimethyl formamide solution (50 μl) containing encapsulated FD40 were added to Milli-Q (3 ml) individually, and stirred well, and FD40 was quantitatively determined by using a fluorescent spectrophotometer (HORIBA, Fluoro MAX-3, excitation wavelength 495 nm, fluorescent wavelength 520 nm), and the encapsulation efficiency in the whole collection volume was calculated.

Figure 13:
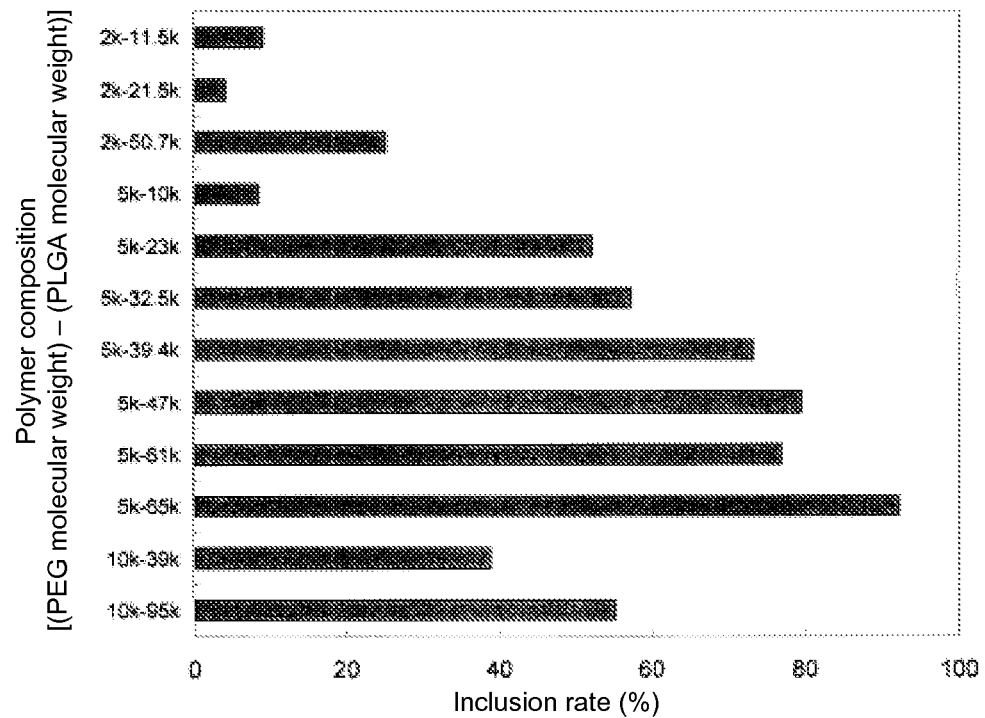
FIG. 13 shows results of enclosure rate entrappement efficiency of FD40 encapsulating microparticles.

FIG. 13 shows the encapsulation efficiency of FD40 in microparticles prepared from PEG-PLGA polymer. In all series of 2k, 5k, 10k of molecular weight of PEG, when the molecular weight of PLG was high, the encapsulation efficiency tended to be high. In particular, in the PEG5k series, at 5k-65k, the encapsulation efficiency was very high, being about 90%. The encapsulation efficiency was about 55% in 10k-95k (PLGA/PEG=9.5) nearly at a same molecular weight ratio as 5k-47k *OKGA/PEG=9.4) of high encapsulation efficiency (about 80%), the encapsulation efficiency was about 55%.

Comparative Example 3

Manufacture of Particles Encapsulating FD40

10 mg of PEG-PLGA polymer (5k-61k) was dissolved in 2 mL of ethyl acetate to prepare a polymer solution. In this polymer solution, 100 μL of 2 mg/mL growth hormone solution was dropped, and stirred. After stirring operation, the solution was added to 20 mL of dioxane. The solvent was evaporated, and concentrated to about 2 mL, and the particle dispersion liquid was added to water containing 500 mg Pluronic F-68 (a registered trademark of BASF). The sample was freeze-dried, and 1 mL of water is added to 50 mg of the sample, and the particles were dispersed again, and non-associated hydrophilic active substance containing particles were obtained. The average particle diameter of the particles was measured by a dynamic light scatter method by using an apparatus ELS-Z (manufactured by Otsuka Denshi), and the drug encapsulation efficiency was determined same as in Example 23.

As a result, the encapsulation efficiency of FD40 was 48%, the average particle diameter was 203.8 nm, and the encapsulation efficiency was lower than in the microparticles of Example 23.

Example 24

Analysis of In-Vitro FD40 Release Speed from Microparticles Encapsulating FD40

To evaluate the relation between the sustained-release behavior and the length of PLGA chain for composing the PEG-PLGA polymer particle, release behavior was evaluated in particles of 5k-23k, 5k-32.5k, 5k-47k, and 5k-61k, out of the microparticles encapsulating the FD40 prepared in Example 22.

Microparticles were, right after preparation, stored in freeze-dried state at −30° C., and returned to normal temperature before use. Exactly 20 mg of particle powder was weighed, and put in a 1.5 ml tube (Eppendorf tube), and 1 ml of assay buffer was added (0.02% sodium azide, 0.1% Pluronic F-68 (a registered trademark of BASF), and 0.1% bovine serum albumin added PBS solution), and stirred firmly by a touch mixer and suspended. Then, using Hitachi high-speed centrifugal machine (CF16RX), the solution was centrifuged for 10 minutes at 18,900×g, and 950 μl of supernatant fraction containing non-encapsulated FD40 was removed, and 950 μl of assay buffer was added again, and the particles were suspended and centrifuged, and the particle cleaning operation was repeated in a total of three times.

In the particles cleaned three times, 950 μl of assay buffer was added once more, and the particles were suspended, and 100 μl each was dispensed in a 1.5 ml tube. In each tube, 900 μl of assay buffer was added to obtain a total solution of 1 ml, which was incubated in an incubator at 37° C. while being rotated at 10 rpm by means of a rotator. Each incubated tube was centrifuged sequentially for 10 minutes at 18900×g, and 950 μl of supernatant was dispended, and stored at 4° C. until the time of measurement of fluorescent intensity.

The fluorescent intensity of the sampled solution was measured by using 3 ml disposal cuvette (KARTELL) and HORIBA Fluoro MAX-3, at excitation wavelength of 494 nm and fluorescent wavelength of 512 nm, and the sustained-release ratio was determined from the ratio of the amount of FD40 used in preparation of particles.

Figure 16:
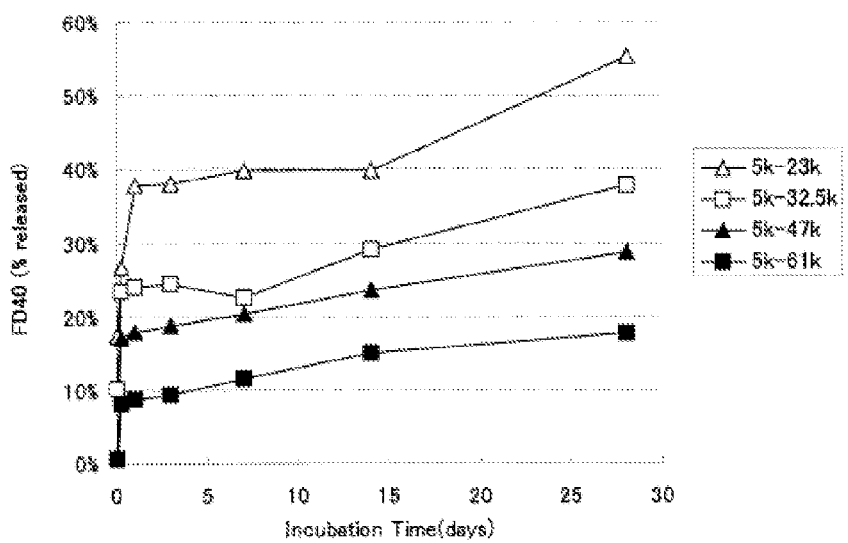
FIG. 16 shows release behavior of FD40 from FD40-encapsulating microparticles.

FIG. 16 shows the release amount of FD40 from the various microparticles determined by the release evaluation. The axis of abscissas denotes the incubation time, and the axis of ordinates represents the release ratio to the charged amount. In 5k-23k particles short in the PLGA chain, about 40% of the charged amount was released within 1 day in the initial period of incubation, and in one month, almost all amount was released except of the portion of initial burst. By contrast, as the length of the PLGA chain becomes longer, the initial release amount decreased, and in microparticles of 5k-61k, the release amount in a first day of initial period of 10% or less.

Example 25

Measurement of Drug Encapsulation Efficiency of Microparticles Encapsulating Human Insulin Using the PEG-PLGA polymer (5k-61k) prepared in Example 20, microparticles encapsulating human insulin were prepared in the same method as in Example 22. Obtained microparticles (20 mg) were weighed by using a 1.5 ml Eppendorf tube, and dissolved in 1 ml of buffer solution A (PBS containing 0.1% bovine serum albumin, 0.1% Pluronic F-68 (a registered trademark of BASF), and 0.02% sodium azide), and were centrifuged for 10 minutes at 18,800×g, and separated into particles (precipitation) and a supernatant. The supernatant was collected in other tube, and the particles were suspended again in 1 ml of buffer solution A, and the centrifugal operation and the separation into particles and a supernatant were conducted again in the same conditions. This cleaning operation was repeated once more (total three times of centrifugal operation), and the human insulin concentration of each supernatant collected by the centrifugal operations was measured by sandwich ELISA method.

The sandwich ELISA method was conducted in the following procedure. Anti-human insulin monoclonal antibody (manufactured by Fitzgerald, clone No. E6E5) was immobilized on an ELISA plate (Maxisorp of Nunc Corp.) at concentration of 5 μg/ml, and 50 μL of ELISA buffer solution (0.1 M Tris chlorate buffer solution containing 0.25% BSA and 0.05% Tween 20, pH 8.0) and 50 μL of measurement sample or standard sample diluted in ELISA diluting solution (PBS containing 0.25% BSA and 0.05% Tween 20) were added, and the solution was reacted at room temperature by shaking for 1 hour. The plate was cleaned three times in a cleaning solution (PBS containing 0.05% Tween 20), and the unreacted reagent was removed, and 0.5 μg/ml of biotin-labeled antihuman monoclonal antibody (manufactured by Fitzgerald, clone No. D4B8), and strepto-avidin-HRP conjugate (manufactured by Zymed) were added, and the solutions were reacted at room temperature by shaking for 1 hour and 15 minutes. After each reaction, the plate was cleaned three times in a cleaning solution (PBS containing 0.05% Tween 20), and the unreacted reagent was removed. Finally, the substrate of HRP was added, and the HRP enzyme activity of the combined conjugate was determined by colorimetry, and on the basis of the working curve prepared from color development of standard insulin, the insulin concentration in the sample was determined.

From the charged amount of human insulin at the time of preparation of particles (per particle weight 20 mg), the human insulin total amount of three supernatants by centrifugal operations was subtracted, and the encapsulation efficiency was calculated according to the formula below:

$$\text{Encapsulation efficiency (\%)} = \frac{(\text{charged insulin amount (ng)} - \text{insulin amount total in supernatants (ng)})}{\text{charged insulin amount (ng)}} \times 100$$

The average particle diameter of the obtained microparticles was 4.7 μm. The encapsulation efficiency of human insulin in microparticles was 86.75, and it was proved that the protein drug could be contained at a high efficiency.

Example 26

Analysis of In-Vitro Drug Release Speed from Microparticles Encapsulating Human Insulin The microparticles centrifuged three times in Example 25 were suspended and dispersed in 1.0 ml of buffer solution A. From this solution, 0.1 ml each was dispensed in ten Eppendorf tubes (1.5 ml capacity), and 0.9 ml of buffer solution A was added in each tube, and diluted 10 times. Right after dilution, one tube was centrifuged for 10 minutes at 18,800×g to precipitate the particles, and a supernatant was collected in a different tube (0-hour sample). The remaining nine tubes were rolled and mixed slowly in an incubator at 37° C., by using a rotator at a speed of 6 rpm. At specific time intervals, each tube was similarly centrifuged, and the supernatant was separated. In the supernatant sample collected at each time, the insulin concentration was measured by the sandwich ELISA method, and the insulin release amount (%) was calculated in the formula below:

$$\text{Release amount (\%)} = \frac{(\text{insulin concentration in supernatant (ng/ml)} \times 1 \text{ (ml)})}{\text{encapsulated insulin amount (ng) in 20 mg of particles}} \times 100.$$

Figure 17:
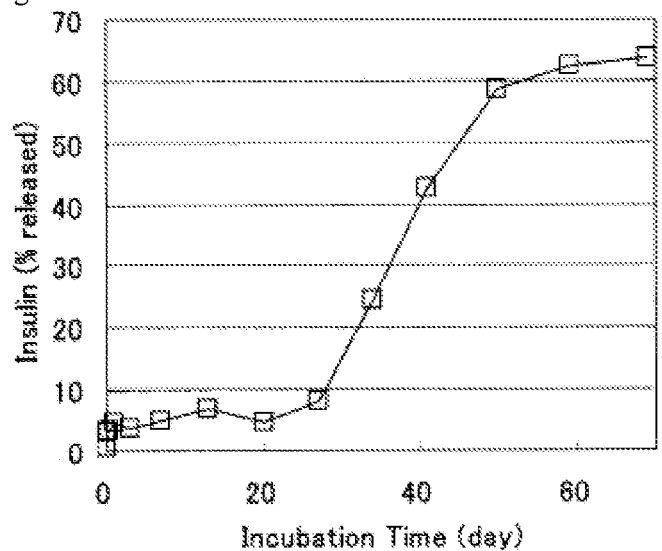
FIG. 17 shows release behavior of drug from human insulin-encapsulating microparticles.

FIG. 17 shows time-course changes of insulin release. Along with the lapse of time, the drug was released gradually, and the release speed increased after 30 days, and the majority of the drug was released in about 60 days.

Example 27

Hypodermic Administration of Microparticles Encapsulating Human Growth Hormone (hGH) in Mouse 25 mg of PEG-PLGA polymer was dissolved in 500 μl of dimethyl carbonate to prepare a polymer solution of 50 mg/ml. In this polymer solution, 100 μl of tert-butanol was added, and 250 μl of 10 mg/ml hGH aqueous solution was dropped, and stirred by vortex to prepare a reversed-phase emulsion. This reversed-phase emulsion was frozen preliminarily by liquid nitrogen, and was freeze-dried by using a freeze-drying apparatus (EYELA, FREEZE DRYER FD-1000), at trap cooling temperature of −45° C., and degree of vacuum of 20 Pa, for 24 hours. The obtained solid content was dispersed in 1 ml of dimethyl carbonate to prepare an S/O suspension. This S/O suspension was dropped in 10 ml of aqueous solution containing 10% Pluronic F-68 (a registered trademark of BASF), and was stirred and emulsified in a vortex mixer to prepare an S/O/W type emulsion. From this S/O/W type emulsion, the water-immiscible organic solvent was removed by drying in liquid, and a microparticle dispersion liquid was obtained. The microparticle dispersion liquid was preliminarily frozen by liquid nitrogen, and was freeze-dried by using a freeze-drying apparatus (EYELA, FREEZE DRYER FD-1000), at trap cooling temperature of −45° C., and degree of vacuum of 20 Pa, for 24 hours, and hGH-encapsulating microparticle powder was obtained. The average particle diameter of the obtained microparticles was 6.0 μm.

300 mg of the prepared microparticles was suspended and dispersed in 3 ml of phosphate physiological buffer solution (PBS), and centrifuged for 5 minutes at 80×g to precipitate microparticles, and a supernatant was transferred into other tube. The supernatant was centrifuged again for 5 minutes at 80×g to precipitate the remaining particles, and the supernatant was removed. The first centrifugal precipitation and the second centrifugal precipitation were combined, and dispersed again in 1 ml of PBS, and the same centrifugal cleaning operation was repeated three times in total, and the growth hormone not encapsulated in the microparticles were removed. Finally, the precipitation was dispersed again in 200 μl of PBS, and an administration solution was obtained. The growth hormone amount encapsulated in PEG-PLGA particles was measured by an ELISA kit, and subtracted from the charged amount, and the amount encapsulated in 300 mg of particles administered per mouse was determined, and 700 μg of PEG-PLGA microparticles was obtained.

This solution was injected hypodermically at two positions in the back of 10-week male Balb/C mouse, and the blood was sampled at specific time intervals from the caudal vein. In the sampled blood, heparin of final concentration of 3.3 IU/ml was added, and plasma was collected by centrifugal separation for 5 minutes at 5,000 rpm, and the concentration of growth hormone in plasma was measured by using an ELISA kit.

By way of comparison, a non-granulated human growth hormone protein solution (700 μg/0.2 ml) was hypodermically administered in mouse, and the blood was sampled similarly.

To suppress antibody production by administration of human growth hormone, which is a foreign protein for mouse, three days before administration of the particle, an immunosuppressant Tacrolimus hydrate (Astellas) was hypodermically administered by 26 μg/mouse, and thereafter 13 μg/mouse was hypodermically administered at the time of the drug administration, and 3 days and 7 days later.

Figure 18:
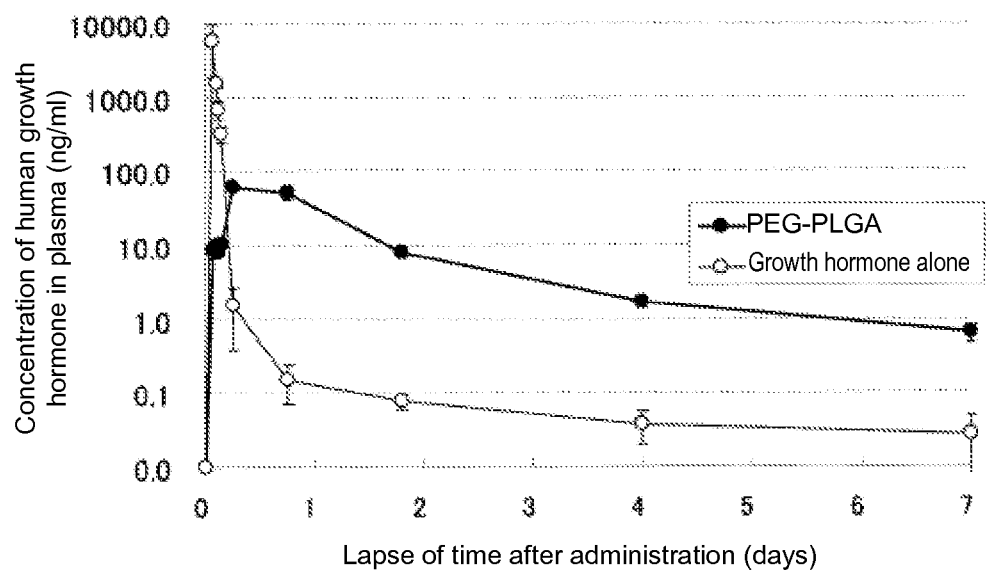
FIG. 18 shows time-course changes of blood drug concentration in mouse administered human growth hormone-encapsulating microparticles subcutaneously.

FIG. 18 shows time-course changes of concentration of human growth hormone in plasma. In the mouse administered non-granulated drug, the blood level in 1 hour after administration was very high, more than 5,000 ng/ml, and then dropped suddenly, to a level before administration in a day. On the other hand, in the mouse administered the microparticle drug prepared by using PEG-PLGA polymer, a transient elevation of blood level right after administration was suppressed to 100 ng/ml or less, and for seven consecutive days, the blood level was sustained at high levels.

Example 28

Manufacture of Microparticles Adding Salt to Liquid Phase in Step (c)

In 100 μl of 50 mg/ml PEG-PLGA polymer (5k-61k)/dimethyl carbonate solution, 20 μl of tert-butanol was added, and 20 μl of 10 mg/ml FD40 aqueous solution was added, and the mixture was stirred to prepare a reversed micelle (W/O emulsion) solution. The obtained solution was frozen preliminarily by liquid nitrogen, and was freeze-dried overnight by using a freeze-drying apparatus, and a solid content containing FD40 was obtained. In the obtained solid content containing FD40, 200 μl of dimethyl carbonate was added, and stirred for 10 second by vortex to prepare an S/O suspension, and it was dropped in 2 ml of aqueous solution containing 10% Pluronic F-68 (a registered trademark of BASF) together with sodium chloride at specified concentration (0 M, 10 mM, 50 mM, 1 M), and was stirred and emulsified by vortex for 30 seconds to prepare an S/O/W type emulsion solution. From the obtained S/O/W type emulsion solution, the water-immiscible organic solvent was removed by using an evaporator (evacuated to 30 hPa, and evacuated and distilled away for 5 minutes) to prepare a water disperse matter of microparticles containing FD40. The disperse aqueous solution of microparticles containing FD40 was frozen preliminarily by liquid nitrogen, and was freeze-dried overnight by using a freeze-drying apparatus, and FD40 containing microparticle powder was obtained. The obtained microparticles were observed by a scanning electron microscope (SEM: HITACHI, S-4800), and the average particle diameter was calculated, and in all sodium chloride concentration conditions, the average particle diameter of microparticles was 6.5 μm.

20 mg of the obtained FD40 containing microparticle powder was weighed, and dispersed in 1 ml of PBS buffer solution (containing 0.1% Pluronic F-68 (a registered trademark of BASF), 0.1% BSA, and 0.01% sodium azide), and centrifuged (14,000 rpm, 10 minutes). After collection of the supernatant, the microparticles were suspended again in 1 ml of PBS buffer solution, and centrifuged, and the microparticles were cleaned further two more times. The cleaned microparticles were suspended again in 1 ml of PBS buffer solution, dispended by 900 μl each in 1.5 ml Eppendorf tubes, and 900 μl of PBS buffer solution was added, and the solution was incubated at 37° C., and samples were collected after 24 hours. The collected samples were centrifuged for 10 minutes at 14,000 rpm, and FD40 contained in the supernatant was measured by using a fluorescent spectrophotometer (HORIBA, Fluoro MAX-3, excitation wavelength 495 nm, fluorescent wavelength 520 nm), and the release amount was calculated. The amount of FD40 in the supernatant collected at the time of cleaning was measured similarly, and the encapsulation efficiency was calculated from the charged amount.

The encapsulation efficiency was 73%, 97%, 84%, and 82% at sodium chloride concentrations of 0 M, 10 mM, 50 mM, and 1 M. The release amount in 1 day was 14%, 7%, 15%, and 11% at sodium chloride concentrations of 0 M, 10 mM, 50 mM, and 1 M, and at the sodium chloride concentration of 10 mM, the encapsulation efficiency was highest, and the release amount in 1 day (initial burst) was least.

Example 29

Hypodermic Administration of Microparticles Encapsulating Human Growth Hormone (hGH) in Mouse (Pharmacological Activity Evaluation)

25 mg each of PEG-PLGA polymer (5k-55k) and PEG-PLGA polymer (5k-105k) of Example 20 was dissolved in 500 μl of dimethyl carbonate to prepare a polymer solution of 50 mg/ml. In this polymer solution, 100 μl of tert-butanol was added, and 250 μl of 10 mg/ml hGH aqueous solution was dropped, and stirred by vortex to prepare a reversed-phase emulsion. This reversed-phase emulsion was frozen preliminarily by liquid nitrogen, and was freeze-dried by using a freeze-drying apparatus (EYELA, FREEZE DRYER FD-1000), at trap cooling temperature of −45° C., and degree of vacuum of 20 Pa, for 24 hours. The obtained solid content was dispersed in 1 ml of dimethyl carbonate to prepare an S/O suspension. This S/O suspension was dropped in 10 ml of aqueous solution containing 10% Pluronic F-68 (a registered trademark of BASF), and was stirred and emulsified in a vortex mixer to prepare an S/O/W type emulsion. From this S/O/W type emulsion, the water-immiscible organic solvent was removed by drying in liquid, and a microparticle dispersion liquid was obtained. The microparticle dispersion liquid was preliminarily frozen by liquid nitrogen, and was freeze-dried by using a freeze-drying apparatus (EYELA, FREEZE DRYER FD-1000), at trap cooling temperature of −45° C., and degree of vacuum of 20 Pa, for 24 hours, and hGH-encapsulating microparticle powder was obtained. The obtained microparticles were observed by a scanning electron microscope (SEM: HITACHI, S-4800), and the average particle diameter was calculated, and the average particle diameter of the obtained microparticles was 4.2 μm in the microparticles from PEG-PLGA polymer (5k-55k) (5k-55k microparticles), and 7.5 μm in the microparticles from PEG-PLGA polymer (5k-105k) (5k-105k microparticles).

300 mg each of the microparticles prepared above was suspended and dispersed in 3 ml of phosphate physiological buffer solution (PBS), and particles were precipitated by centrifugal separation for 5 minutes at 80×g, and a supernatant was transferred in other tube. The supernatant was centrifugally separated again for 5 minutes at 80×g, and the remaining particles were precipitated, and the supernatant was removed. The first centrifugal precipitation and the second centrifugal precipitation were combined, and dispersed again in 1 ml of PBS, and similarly a third centrifugal operation was conducted, and the growth hormone not encapsulated in the particles was removed. Finally, the precipitation was dispersed again in 200 µl of PBS to prepare an administration solution.

This solution was hypodermically injected in the back of 8-week-old pituitary gland extracted ICR mouse (from Japan SLC), and the blood was sampled at specific intervals from the caudal vein. In the sampled blood, heparin of final concentration of 3.3 IU/ml was added, and centrifuged for 5 minutes at 5,000 rpm, and the plasma was collected, and the growth hormone concentration in plasma and the mouse IGF-1 concentration were measured by ELISA method.

By way of comparison, a non-granulated human growth hormone protein solution (700 µg/0.2 ml) was hypodermically administered in mouse, and the blood was sampled similarly.

To suppress antibody production by administration of human growth hormone, which is a foreign protein for mouse, three days before administration of the particle, an immunosuppressant Tacrolimus hydrate (Astellas) was hypodermically administered by 26 µg/mouse, and thereafter 13 µg/mouse was hypodermically administered at the time of the drug administration, and twice a week thereafter.

Figure 19:
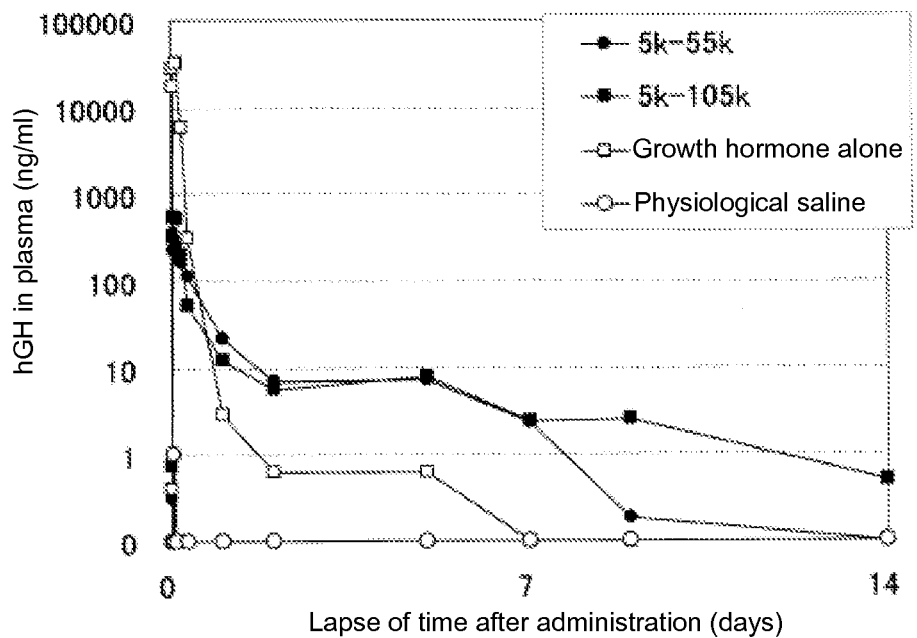
FIG. 19 shows time-course changes of blood drug concentration in mouse administered human growth hormone-encapsulating microparticles subcutaneously.

FIG. 19 shows time-course changes of concentration of human growth hormone in plasma. In the mouse administered non-granulated drug, the blood level in 1 hour after administration was very high, and then dropped suddenly, to a level before administration in one day. On the other hand, in the mouse administered the microparticle drug manufactured by using PEG-PLGA polymer, a transient concentration elevation right after administration was suppressed low, about $1/100$ of the level in the mouse administered non-granulated drug, and for more than nine consecutive days after administration, the blood level was sustained at high levels.

Figure 20:
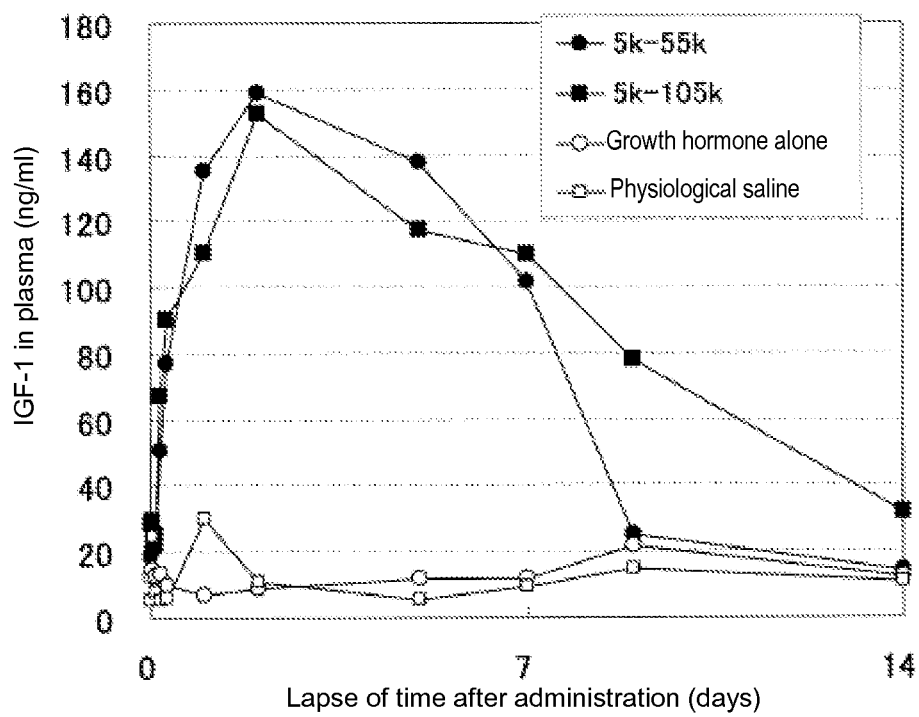
FIG. 20 shows time-course changes of blood IGF-1 concentration in mouse administered human growth hormone-encapsulating microparticles subcutaneously.

FIG. 20 shows the IGF-1 concentration in plasma during this time period. The IGF-1 concentration in plasma was elevated after administration in both 5k-55k microparticles and 5k-105k microparticles, and high levels were maintained for 7 days in 5k-55k microparticles, and more than 14 days in 5k-105k microparticles.

Example 30

Hypodermic Administration of Microparticles Encapsulating Exendin-4 (GLP-1 Receptor Agonist) in Mouse 25 mg of PEG-PLGA polymer (5k-61k) in Example 20 was dissolved in 500 µl of dimethyl carbonate to prepare a polymer solution of 50 mg/ml. In this polymer solution, 100 µl of tert-butanol was added, and 250 µl of 10 mg/ml Exendin-4 (synthesized by commission with Sigma Genosys) was dropped, and stirred by vortex to prepare a reversed-phase emulsion. This reversed-phase emulsion was frozen preliminarily by liquid nitrogen, and was freeze-dried by using a freeze-drying apparatus (EYELA, FREEZE DRYER FD-1000), at trap cooling temperature of −45° C., and degree of vacuum of 20 Pa, for 24 hours. The obtained solid content was dispersed in 1 ml of dimethyl carbonate to prepare an S/O suspension. This S/O suspension was dropped in 10 ml of aqueous solution containing 10% Pluronic F-68 (a registered trademark of BASF), and was stirred and emulsified in a vortex mixer to prepare an S/O/W type emulsion. From this S/O/W type emulsion, the water-immiscible organic solvent was removed by drying in liquid, and a microparticle dispersion liquid was obtained. The microparticle dispersion liquid was preliminarily frozen by liquid nitrogen, and was freeze-dried by using a freeze-drying apparatus (EYELA, FREEZE DRYER FD-1000), at trap cooling temperature of −45° C., and degree of vacuum of 20 Pa, for 24 hours, and Exendin-4-encapsulating microparticle powder was obtained. The obtained microparticles were observed by a scanning electron microscope (SEM: HITACHI, S-4800), and the average particle diameter was calculated, and the average particle diameter of microparticles was 6.0 µm.

300 mg of the prepared microparticles was suspended and dispersed in 3 ml of phosphate physiological buffer solution (PBS), and particles were precipitated by centrifugal separation for 5 minutes at 80×g, and a supernatant was transferred in other tube. The supernatant was centrifugally separated again for 5 minutes at 80×g, and the remaining particles were precipitated, and the supernatant was removed. The first centrifugal precipitation and the second centrifugal precipitation were combined, and dispersed again in 1 ml of PBS, and similarly a third centrifugal operation was conducted, and the Exendin-4 not encapsulated in the particles was removed. Finally, the precipitation was dispersed again in 200 µl of PBS to prepare an administration solution.

This solution was injected hypodermically at two positions in the back of 10-week male Balb/C mouse (from Japan SLC), and the blood was sampled at specific time intervals from the caudal vein. In the sampled blood, heparin of final concentration of 3.3 IU/ml was added, and plasma was collected by centrifugal separation for 5 minutes at 5,000 rpm, and the concentration of growth hormone in plasma was measured by the ELISA method.

By way of comparison, a non-granulated Exendin-4 solution (700 µg/0.2 ml) was hypodermically administered in mouse, and the blood was sampled similarly.

To suppress antibody production by administration of Exendin-4, which is a dissimilar protein for mouse, three days before administration of the particle, an immunosuppressant Tacrolimus hydrate (Astellas) was hypodermically administered by 26 µg/mouse, and thereafter 13 µg/mouse was hypodermically administered at the time of the drug administration, and twice a week thereafter.

Figure 21:
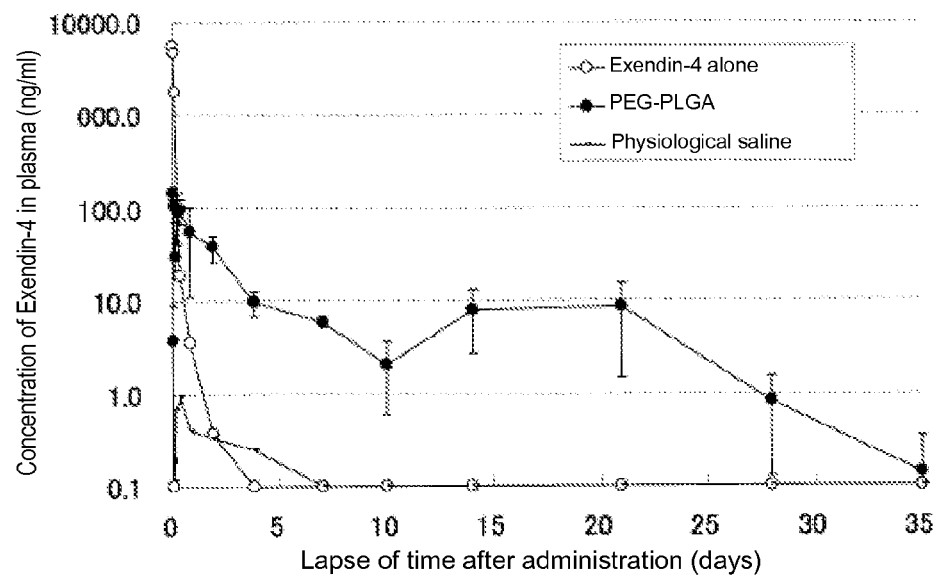
FIG. 21 shows time-course changes of blood pharmacokinetics in mouse administered Exendin-4-encapsulating microparticles subcutaneously.

FIG. 21 shows time-course changes of Exendin-4 concentration in plasma. In the mouse administered non-granulated drug, the blood level in 1 hour after administration was very high, and then dropped suddenly, to a level before administration in a day. On the other hand, in the mouse administered the microparticle drug prepared by using PEG-PLGA polymer, a transient elevation of blood level right after administration was suppressed to about less than $1/100$, and the blood level was sustained at high levels for a month.

Example 31

Preparation of Microparticles Encapsulating Fluoresceine Labeled Dextran (FD40) Different in Particle Diameter 5 mg of PEG-PLGA polymer (5k-55k) in Example 20 was dissolved in 100 µl of dimethyl carbonate to prepare a polymer solution of 50 mg/ml. In this polymer solution, 20 µl of tert-butanol was added, and 20 µl of 1 mg/ml FD40 aqueous solution was dropped, and stirred by vortex to prepare a reversed-phase emulsion. This reversed-phase emulsion was frozen preliminarily by liquid nitrogen, and was freeze-dried by using a freeze-drying apparatus (EYELA, FREEZE DRYER FD-1000), at trap cooling temperature of −45° C., and degree of vacuum of 20 Pa, for 24 hours. The obtained solid content was dispersed in 50 µl, 200 µl, and 500 µl of dimethyl carbonate to prepare an S/O suspension. This S/O suspension was dropped in 2 ml of aqueous solution containing 10% Pluronic F-68 (a registered trademark of BASF), and was stirred and emulsified in a vortex mixer to prepare an S/O/W type emulsion. From this S/O/W type emulsion, the water-immiscible organic solvent was removed by drying in liquid, and a microparticle dispersion liquid was obtained. The microparticle dispersion liquid was preliminarily frozen by liquid nitrogen, and was freeze-dried by using a freeze-drying apparatus (EYELA, FREEZE DRYER FD-1000), at trap cooling temperature of −45° C., and degree of vacuum of 20 Pa, for 24 hours, and FD40-encapsulating microparticle powder was obtained. The obtained microparticles were observed by a scanning electron microscope (SEM: HITACHI, S-4800), and the average particle diameter was calculated.

Figure 22:
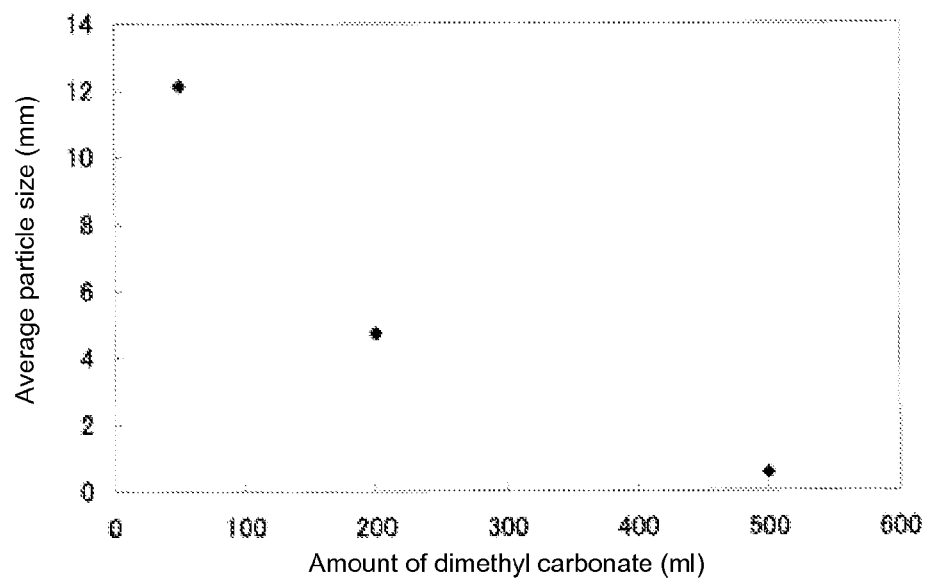
FIG. 22 shows the relation between particle diameter and amount of dimethyl carbonate added at the time of preparation of S/O/W type emulsion.

FIG. 22 shows the correlation between the average particle diameter and the amount of dimethyl carbonate added at the time of preparation of S/O/W type emulsion. In a range from 50 µl to 500 µl, along with increase of dimethyl carbonate amount, decline of the average particle diameter was observed.

INDUSTRIAL APPLICABILITY

A microparticle releases a hydrophilic active substance at an appropriate speed in the human body, and is useful as a DDS pharmaceutical preparation.

The invention claimed is:

1. A microparticle comprising, an agglomerate of bonded hydrophilic active substance containing particles, wherein said particles a) comprise an amphiphilic polymer composed of a poly(hydroxyl acid) hydrophobic segment and a polysaccharide or polyethylene glycol hydrophilic segment; b) contain a hydrophilic active substance, c) remain bonded as agglomerates in a dispersed state in a dispersion medium.

2. The microparticle according to claim 1, wherein the hydrophilic active substance containing particle has an inner hydrophilic segment of amphiphilic polymer, and an outer layer of a hydrophobic segment of amphiphilic polymer.

3. The microparticle according to claim 1, wherein the amphiphilic polymer is a graft amphiphilic polymer composed of a polysaccharide main chain and poly(hydroxy acid) graft chain(s).

4. The microparticle according to claim 3, wherein the polysaccharide main chain is dextran.

5. The microparticle according, to claim 1, wherein the amphiphilic polymer is a block polymer composed of polyethylene glycol and poly(hydroxy acid).

6. The microparticle according to claim 5, wherein the average molecular weight of polyethylene glycol is 2,000 to 15,000.

7. The microparticle according to claim 5, wherein a ratio of average molecular weight of poly(hydroxy acid) to average molecular weight of polyethylene glycol is 4 or more.

8. The microparticle according to claim 1, wherein the poly(hydroxy acid) is poly(lactic acid-glycolic acid).

9. The microparticle according to claim 1, wherein average particle diameter is 1 to 50 µm.

10. The microparticle according to claim 1, wherein the hydrophilic active substance is peptide or a protein.

11. A method for manufacturing a microparticle comprising:
    (a) forming a reversed-phase emulsion by mixing an aqueous solvent containing a hydrophilic active substance and a water-immiscible organic solvent dissolving an amphiphilic polymer composed of a hydrophobic segment of poly(hydroxyl acid) and a hydrophilic segment of polysaccharide or polyethylene glycol,
    (b) obtaining a solid content containing a hydrophilic active substance by removing the solvent from the reversed-phase emulsion, and
    (c) introducing a dispersion liquid containing the solid content into a liquid phase containing a surface modifier, wherein the dispersion liquid is a water-immiscible organic solvent to form the microparticle comprising an agglomerate of bonded particles which remain bonded as the agglomerate in a dispersed state in the dispersion liquid.

12. The method according to claim 11, wherein the solvent is removed from the reversed-phase emulsion by a freeze-drying method.

13. The method according to claim 11, wherein a dispersion medium of the dispersion liquid containing the solid content is a solvent capable of dissolving poly(hydroxy acid) and being 10 mg/mL or less in solubility of a hydrophilic segment for composing an amphiphilic polymer.

14. The method according to claim 11, wherein the liquid phase is either an aqueous solvent or a water miscible organic solvent.

15. A pharmaceutical preparation comprising the microparticle of claim 1.

16. The microparticle according to claim 2, wherein the amphiphilic polymer is a graft amphiphilic polymer composed of a polysaccharide main chain and poly(hydroxy acid) graft chain(s).

17. The microparticle according to claim 2, wherein the amphiphilic polymer is a block polymer composed of polyethylene glycol and poly(hydroxy acid).

18. The microparticle according to claim 2, wherein a ratio of average molecular weight of poly(hydroxy acid) to average molecular weight of polyethylene glycol is 4 or more.

19. The method according to claim 12, wherein a dispersion medium of the dispersion liquid containing the solid content is a solvent capable of dissolving poly(hydroxy acid) and being 10 mg/mL or less in solubility of a hydrophilic segment for composing an amphiphilic polymer.

20. A spherical microparticle comprising an agglomerate of bonded hydrophilic active substance containing particles, which particles comprise an amphiphilic polymer composed of a hydrophobic segment of poly(hydroxyl acid) and a hydrophilic segment of polysaccharide or polyethylene glycol, and a hydrophilic active substance, wherein the particles remain bonded as agglomerates in a dispersed state in a dispersion medium.

21. The microparticle according to claim 1, wherein the microparticle slowly dissolves in a medium and gradually releases the active substance.

22. The method according to claim 11, wherein the microparticle slowly dissolves in a medium and gradually releases the active substance.

* * * * *